US009747424B2

(12) United States Patent
Sablinski

(10) Patent No.: US 9,747,424 B2
(45) Date of Patent: Aug. 29, 2017

(54) SYSTEMS AND METHODS FOR DRUG DEVELOPMENT

(71) Applicant: TRANSPARENCY LIFE SCIENCE, LLC, New York, NY (US)

(72) Inventor: Tomasz Sablinski, Short Hills, NJ (US)

(73) Assignee: Transparency Life Science, LLC, New York, NY (US)

( * ) Notice: Subject to any disclaimer, the term of this patent is extended or adjusted under 35 U.S.C. 154(b) by 108 days.

(21) Appl. No.: 13/751,413

(22) Filed: Jan. 28, 2013

(65) Prior Publication Data

US 2013/0197894 A1    Aug. 1, 2013

Related U.S. Application Data

(63) Continuation-in-part of application No. 13/679,242, filed on Nov. 16, 2012, now abandoned.

(60) Provisional application No. 61/561,445, filed on Nov. 18, 2011, provisional application No. 61/591,464, filed on Jan. 27, 2012.

(51) Int. Cl.
*G06Q 50/22* (2012.01)
*G06Q 50/24* (2012.01)
*G06F 19/00* (2011.01)

(52) U.S. Cl.
CPC ................. *G06F 19/363* (2013.01)

(58) Field of Classification Search
CPC ........ G06Q 50/22; G06Q 50/24; G06Q 10/06; G06Q 10/0633
USPC ......................................................... 705/2, 3
See application file for complete search history.

(56) References Cited

U.S. PATENT DOCUMENTS

| 6,108,635 | A * | 8/2000 | Herren et al. ............... 705/2 |
| 2004/0093240 | A1 | 5/2004 | Shah |
| 2006/0184493 | A1 | 8/2006 | Shiffman et al. |
| 2007/0067189 | A1 | 3/2007 | Boris et al. |
| 2007/0239464 | A1 | 10/2007 | Carroll |

(Continued)

FOREIGN PATENT DOCUMENTS

| JP | 2002-007401 A | 1/2002 |
| WO | WO 2013/074922 A1 | 5/2013 |

OTHER PUBLICATIONS

ISR-WO dated Mar. 8, 2013 cited in PCT/US2012/065514, corresponding to co-pending U.S. Appl. No. 13/679,242.

(Continued)

*Primary Examiner* — Maroun Kanaan
(74) *Attorney, Agent, or Firm* — Wolf, Greenfield & Sacks, P.C.

(57) ABSTRACT

Systems and methods are provided for drug development under a fully transparent development model. The model is configured to provide transparency to the patients, the researchers, clinicians, physicians, and any other registered users of the system who wish to contribute. According to various embodiments, the system and model enable drug development that leverage the combined wisdom and insight of the user population eliminating many of the drawbacks of conventional development approaches. In one embodiment, the system includes drug development engine configured to manage execution of parameters of a clinical trial, including collection of health and treatment information from a patient population. The development engine can publish collected execution data for review and analysis.

30 Claims, 18 Drawing Sheets

(56) References Cited

U.S. PATENT DOCUMENTS

| | | |
|---|---|---|
| 2009/0247836 A1 | 10/2009 | Cole et al. |
| 2009/0281830 A1 | 11/2009 | McNames et al. |
| 2010/0088245 A1 | 4/2010 | Harrison |
| 2010/0138235 A1 | 6/2010 | Marks et al. |
| 2010/0211411 A1 | 8/2010 | Hudson |
| 2010/0324936 A1* | 12/2010 | Vishnubhatla et al. .......... 705/3 |
| 2011/0153361 A1 | 6/2011 | Hanina et al. |
| 2013/0132112 A1 | 5/2013 | Sablinski et al. |
| 2013/0197894 A1 | 8/2013 | Sablinski |

OTHER PUBLICATIONS

PCT Publication PCT/US2012/065514—May 23, 2013—WO2013/074922.

U.S. Appl. No. 13/679,242, filed Nov. 16, 2012, Sablinski et al.

EP 12850297.8, Jun. 1, 2015, Supplemental Extended European Search Report.

PCT/US2012/065514, May 30, 2014, International Preliminary Report on Patentablity.

Supplemental Extended European Search Report mailed Jun. 1, 2015 in connection with European Application No. 12850297.8.

International Preliminary Report on Patentability mailed May 30, 2014 in connection with International Application No. PCT/US2012/065514.

Mintz, Crowdsourcing pharma drug development. Business Development & Licensing Journal. Sep. 2011; 16:12-7.

Sablinksi et al., Crowdsourcing Clinical Drug Development in a transparent model. Open Science Summit Oct. 23, 2011. Retrieved from the Internet on May 21, 2015 at http://diyhpl.us/~bryan/irc/open-science-summit-2011/ 10 21 transparency life sciences.ppt. pp. 9, 14, 15.

Sablinksi, Crowd-Sourcing in Clinical Development. Biopharm Physicians. Jul. 25, 2011; pp. 1-3. Retrieved from the Internet on May 21, 2015 at http://www.biopharmphysicians.com/crowd-sourcing-in-clinical-development/.

Takagari, How to create and revise a protcol of the clinical trials in the pharmaceutical companies—The true intension and the public position. Aug. 23, 2003. pp. 1-5. http://www.csp.or.jp/cspor/upload_files/arch_18.pdf.

* cited by examiner

FIG. 11

Account Information

1202 — Username* ☐
1204 — E-mail address* ☐

1206 — Password* ☐
1208 — Confirm password* ☐
1210 — Therapeutic Area* ☐

Suggest a Question or Comment
Question or Comment
☐

Your E-mail Address
☐

Personal Information

1212 — First Name* ☐
1216 — Middle Initial* ☐
1214 — Last Name* ☐
1218 — Suffix(e.g., Jr., Sr.,) ☐
1220 — Salutation ☐
1222 — Phone Number ☐
1224 — Degrees(s) earned (e.g., MD, PhD) ☐
1226 — Job Title ☐

SUBMIT

Profile Image
Upload [Browse] — 1228

Role
The role(s) you play in drug development  [-select role-] — 1230

SUBMIT — 1232

1402 — Researcher Challenges
1404 — Patient Challenges
1400

Page 1 of 3    Next >

1406 — 🔍 CHALLENGE-1 CLINICAL STUDY POPULATION

▷ Which patient population should be studied initially ?*

1408:
- Clinically Isolated Syndrome — 1410    ○ Yes  ○ No
- Relapsing Remitting — 1411    ○ Yes  ○ No
- Primary Progressive — 1412    ○ Yes  ○ No
- Secondary Progressive — 1413    ○ Yes  ○ No
- Progressive - Relapsing — 1414    ○ Yes  ○ No 1416 — Provide Your Reasoning*

Please describe your reasoning here

1420 — 🔍 CHALLENGE 2 — REGULATORY STRATEGY

▷ Development Path

1422 — Could Linosipril be developed for MS using the 505(b)2 path?    ○ Yes  ○ No

1424

Provide Your Reasoning*

1426

Page 1 of 3    Next >
TOP
1430

| Researcher Challenges | Patient Challenges |

Page 3 of 3                                    < Previous

🔍 CHALLENGE-5 CLINICAL STUDY POPULATION

▷ What strategic factors should be considered?

| Questions1 | ⦿ Yes | ○ No |
| Questions2 | ○ Yes | ⦿ No |
| Questions3 | ⦿ Yes | ○ No |
| Question4  | ○ Yes | ⦿ No |

▷ What strategic factors should be considered?

| Questions1 | ○ Yes | ⦿ No |
| Questions2 | ⦿ Yes | ○ No |
| Questions3 | ○ Yes | ⦿ No |
| Question4  | ⦿ Yes | ○ No |

🔍 CHALLENGE-6 CLINICAL STUDY POPULATION

▷ What strategic factors should be considered?

| Questions1 | ⦿ Yes | ○ No |
| Questions2 | ○ Yes | ⦿ No |
| Questions3 | ○ Yes | ⦿ No |
| Question4  | ○ Yes | ⦿ No |

Page 3 of 3                          < Previous | Submit

FIG. 15

SYSTEMS AND METHODS FOR DRUG DEVELOPMENT

RELATED APPLICATIONS

This application is a continuation-in-part of, and claims priority under 35 U.S.C. §120 to U.S. application Ser. No. 13/679,242, entitled "SYSTEMS AND METHODS FOR CLINICAL PROTOCOL DEVELOPMENT," filed on Nov. 16, 2012, which claims priority under 35 U.S.C. §119(e) to U.S. Provisional Application No. 61/561,445, entitled "SYSTEMS AND METHODS FOR CLINICAL PROTOCOL DEVELOPMENT," filed on Nov. 18, 2011, both of which applications are incorporated herein by reference in their entirety, and this application claims priority under 35 U.S.C. §119(e) to U.S. Provisional Application No. 61/591,464, entitled "SYSTEMS AND METHODS FOR DRUG DEVELOPMENT," filed on Jan. 27, 2012, which application is incorporated herein by reference in its entirety.

BACKGROUND

Currently there exists a need for improvement in conventional methodologies of drug development. According to some conventional approaches, overemphasis on existing FDA approved methodologies has magnified the costs of developing and approving drug candidates. Overemphasis on the marketability of drug candidates has further limited the field of viable drug candidates. Often, bio-pharma market participants have focused on secrecy and market returns to the exclusion of other developments, for example, in pursuing business process efficiencies through implementation of new technology, leveraging industry-wide knowledge, and other non-conventional sources of knowledge. These market participants have developed isolated approaches for drug development composed by a handful of key opinion leaders (who are costly to engage and often replicate procedures for the last FDA-approved drug) and have executed the same approaches over years.

SUMMARY

It is realized that a paradigm shift in conventional approaches to drug development is required. New approaches to drug development are needed that involve those stakeholders who have chronically been under-represented in conventional systems. Further, there exists a need for better focused drug development approaches that reduce execution cost and execution time without regard to the scope of the marketplace for a drug candidate.

According to one aspect, it is realized that it is advantageous to involve as many individuals from any one or more of trial patients, researchers, and other stakeholders at the earliest phases of the development of a drug protocol or trial. Such individuals in particular patients and their relatives or doctors can contribute an unique understanding of their own illnesses and a unique understanding of the physical characteristics that measure their health in terms of their illness. In addition, researchers can contribute insights into clinical trial parameters based on their unique understanding of disease states, experimental design, and data analysis. According to some aspects, a drug development system is implemented under a partial and preferably fully transparent development model. The model is configured to provide transparency to the patients, transparency to the researchers, transparency to other clinicians, physicians, and other registered users of the system. According to various embodiments, the system and model enable drug development without many of the drawbacks of conventional approaches.

Stated broadly, various aspects relate to systems and methods that are configured to provide a systemic solution to the crisis in drug development. Specifically, some embodiments disclosed herein enable a combination of various components and solutions/methods that provide several benefits and improvements. Benefits can include an improvement of understanding of methodologies of drug development, an increased interest of patients to participate in clinical studies, a higher quality of drug development plans, a significantly higher convenience for patients participating in clinical studies, a significantly higher speed of drug development can be realized, particularly in clinical studies, and a significant decrease of costs of drug development, particularly in clinical studies.

Other benefits can also be attained according to other implementations and/or embodiments. According to some embodiments, patient retention rates are expected to improve by generating more meaningful studies (from patient perspective as well as the perspective of other participants). Further embodiments are expected to improve retention rates by keeping the communication lines open between patients and researchers. In other embodiments, remote collection at a patient's home reduces costs, improves compliance, and reduces patient drop-out.

According to one aspect, a drug development system implementing a transparent development model is provided. The system comprises at least one processor operatively connected to a memory, the at least one processor when executing provides a protocol builder subsystem configured to define a clinical trial, wherein the protocol builder subsystem is configured to define parameters of the clinical trial responsive to input from registered users, and wherein the protocol builder subsystem is configured to publish the input received on the parameters for the clinical trial for access on the drug development system, a drug development engine configured to manage execution of the parameters of the clinical trial, wherein the drug development engine includes, a collection component configured to receive remote trial execution data, wherein the collection component is configured to receive at least health and treatment information from a patient population defined for the clinical trial, and a user interface configured to publish at least a portion of the trial execution data for review on the drug development system, and wherein the user interface is configured to accept and publish user input regarding the at least the portion of the trial execution data.

According to one embodiment, the user interface includes a registration component configured to register a plurality of users including at least patients and trial investigators. According to one embodiment, the protocol builder subsystem is configured to generate survey questions presented to the plurality of registered users to define at least one parameter of the clinical trial. According to one embodiment, the survey questions are configured to define patient priorities regarding clinical end-points for execution of the clinical trial. According to one embodiment, the protocol builder subsystem is further configured to define at least one clinical end-point parameter responsive to the patient priorities established by the survey questions. According to one embodiment, the survey questions are configured to define researcher priorities regarding clinical end-points for execution of the clinical trial. According to one embodiment, the protocol builder subsystem is further configured to define at least one clinical end-point parameter responsive to the researcher priorities established by the survey questions.

According to one embodiment, the user interface component is configured to publish the at least the portion of the trial execution data for review on the drug development system during execution of the clinical trial.

According to one embodiment, the system further comprises an analysis component configured to aggregate the remote trial execution data to generate the at least the portion of the remote trial execution data. According to one embodiment, the system further comprises a storage component configured to store remote trial execution data with an associated patient. According to one embodiment, the user interface is configured to display the remote trial execution data associated with the patient to the patient responsive to authentication. According to one embodiment, the user interface is configured to accept user submissions regarding the at least the portion of the remote trial execution data. According to one embodiment, the user interface is configured to publish the user submissions regarding the at least the portion of the remote trial execution data.

According to one embodiment, the system further comprises an analysis component configured to identify indicators for altering at least one parameter defined for the clinical trial, responsive, at least in part to the user submissions. According to one embodiment, the analysis component is configured to identifying indicators for terminating the execution of the clinical trial early responsive, at least in part, to one or more of the user submissions and the remote execution data.

According to one aspect, a computer implemented method for transparent drug development is provided. The method comprises defining, by a computer system, a clinical trial, wherein defining the clinical trial includes defining parameters of the clinical trial responsive to input from registered users, publishing, by the computer system, the input received on the parameters for the clinical trial for review on the computer system, managing, by the computer system, execution of the parameters of the clinical trial, wherein managing execution includes receiving remote trial execution data from at least health and treatment monitoring devices associated with a patient population defined for the clinical trial, and publishing, by the computer system, at least a portion of the remote trial execution data for review on the drug development system.

According to one embodiment, publishing, by the computer system, at least a portion of the remote trial execution data includes publishing the at least the portion of the remote trial execution data during execution of the clinical trial. According to one embodiment, the method further comprises aggregating, by the computer system, the execution data to generate the at least the portion of the remote trial execution data for review. According to one embodiment, the method further comprises generating survey questions presented to a plurality of registered users, and defining at least one parameter of the clinical trial responsive to answers to the survey questions. According to one embodiment, the survey questions are configured to define patient priorities regarding clinical end-points for execution of the clinical trial. According to one embodiment, defining the at least one parameter of the clinical trial responsive to answers to the survey questions includes defining the at least one clinical end-point parameter responsive to the patient priorities established by the survey questions. According to one embodiment, the survey questions are configured to define researcher priorities regarding clinical end-points for execution of the clinical trial. According to one embodiment, defining the at least one parameter of the clinical trial responsive to answers to the survey questions includes defining the at least one clinical end-point parameter responsive to the researcher priorities established by the survey questions.

According to one embodiment, the method further comprises identifying a clinical trial patient responsive to user input, and presenting the remote trial execution data associated with the clinical trial patient responsive to identification. According to one embodiment, the method further comprises accepting user submissions regarding the at least the portion of the remote trial execution data. According to one embodiment, the method further comprises publishing, by the computer system, the user submissions regarding the portion of the remote trial execution data for review on the drug development system. According to one embodiment, the method further comprises altering at least one parameter defined for the clinical trial responsive, at least in part, to the user submissions. According to one embodiment, the method further comprises identifying indicators for terminating the execution of the clinical trial early responsive, at least in part, to one or more of the user submissions and the remote execution data.

According to one embodiment, the method further comprises managing, by the computer system, virtual interviews between clinical investigators and the clinical trial population according to the parameters of the clinical trial.

According to one aspect, provided is a non-transitory computer-readable medium having computer-readable signals stored thereon that define instructions that, as a result of being executed by a computer, instruct the computer to perform the method for transparent drug development. The method comprises defining, by a computer system, a clinical trial, wherein defining the clinical trial includes defining parameters of the clinical trial responsive to input from registered users, publishing, by the computer system, the input received on the parameters for the clinical trial for review on the computer system, managing, by the computer system, execution of the parameters of the clinical trial, wherein managing execution includes receiving remote trial execution data from at least health and treatment monitoring devices associated with a patient population defined for the clinical trial, and publishing, by the computer system, at least a portion of the remote trial execution data for review on the drug development system.

According to one embodiment, publishing, by the computer system, at least a portion of the remote trial execution data includes publishing the at least the portion of the remote trial execution data during execution of the clinical trial. According to one embodiment, the method further comprises aggregating, by the computer system, the execution data to generate the at least the portion of the remote trial execution data for review. According to one embodiment, the method further comprises generating survey questions presented to a plurality of registered users, and defining at least one parameter of the clinical trial responsive to answers to the survey questions. According to one embodiment, the survey questions are configured to define patient priorities regarding clinical end-points for execution of the clinical trial. According to one embodiment, defining the at least one parameter of the clinical trial responsive to answers to the survey questions includes defining the at least one clinical end-point parameter responsive to the patient priorities established by the survey questions. According to one embodiment, the survey questions are configured to define researcher priorities regarding clinical end-points for execution of the clinical trial. According to one embodiment, defining the at least one parameter of the clinical trial responsive to answers to the survey questions includes defining the at least one clinical end-point parameter responsive to the researcher priorities established by the survey questions.

According to one embodiment, the method further comprises identifying a clinical trial patient responsive to user input, and presenting the remote trial execution data associated with the clinical trial patient responsive to identification. According to one embodiment, the method further comprises accepting user submissions regarding the at least the portion of the remote trial execution data. According to one embodiment, the method further comprises publishing, by the computer system, the user submissions regarding the portion of the remote trial execution data for review on the drug development system. According to one embodiment, the method further comprises altering at least one parameter defined for the clinical trial responsive, at least in part, to the user submissions. According to one embodiment, the method further comprises identifying indicators for terminating the execution of the clinical trial early responsive, at least in part, to one or more of the user submissions and the remote execution data.

According to one embodiment, the method further comprises managing, by the computer system, virtual interviews between clinical investigators and the clinical trial population according to the parameters of the clinical trial.

Various aspects relate to the development of clinical study (a.k.a. trial) protocols in drug development. In some settings, the trial development process can be optimized by integrating and receiving feedback from a large number of participants (physicians, researchers, technicians, drug developers, patients, etc.). Some embodiments invoke the combined wisdom of the user population by targeting relevant audiences for feedback and input into clinical study protocol development. User input can be solicited and developed in an open format, allowing the system to capture the largest possible knowledge base regarding protocol development.

In some settings, a set of "protocol challenges" are presented by a protocol builder system to a global community of drug developers, scientists, physicians, and patients to develop and identify issues with a clinical study protocol. A clinical study protocol represents the collection of some and preferably all aspects of a specific scientific experiment, which is part of a broader development path for a new drug or therapy. The scientific experiment can define patient population by inclusion characteristics (e.g., males age 50+), a drug to administer, including dosage, timed release or not, a placebo to administer to subjects in a control group, size of the study population, exclusion criteria (e.g., no existing heart conditions). Protocol challenges can be used to identify the best set of criteria for a given clinical study protocol ("protocol").

The system can be configured to ask participating individuals to respond to questions identified with the protocol challenges. Each challenge can be composed of individual or groups of questions. In some embodiments, the questions include both multiple choice and open-response interfaces for accepting answers. In one embodiment, the system provides for protocol challenges based on drug candidates in specific indications by posing challenge questions directly pertaining to key clinical study parameters: including research methods, study population, statistical analysis, study design, study procedures, and potential adverse events.

In one aspect, the system includes a curated environment implemented over a public network (e.g., the Internet) for rapid design of scientific experiments within or encompassing a clinical study. The curated environment includes, for example, a research or patient advocate assigned to review and/or approve postings and submissions within the environment. In some embodiments, the research or patient advocate can act as the curator in the curated environment. As the scientific experiments being developed can include human trials, the research or patient advocate can review any suggested experiment for safety, impact, quality, deviation from conventional medical approach, and effect on study participants of the scientific experiment being developed among other options.

Some scientific experiments are constructed for testing unproven clinical treatments in humans. In one example, the curated environment solicits user input through interactive surveys. Some embodiments employ the feedback delivered by the interactive surveys to optimize the development of a clinical study protocol. In one example, the curated environment allows for significant reduction in development time over some conventional trial development methodologies. User surveys can be targeted to a particular user population and the resulting information collected to allow the system to quickly evaluate and enhance, for example, a drug development plan or a therapeutic approach. In some embodiments, the system is configured to provide for evaluation of user submissions for compensation. According to one embodiment, an evaluation process is described that provides fair, equitable, and timely rewards to users free of any bias. Unbiased and fair compensation serves the system by encouraging participants to submit their ideas. Unbiased and fair compensation can also serve the system by encouraging continued participation.

In some embodiments, the highest scoring submissions can be identified from submissions of a large number of registered participants. The large number of participants can include invited participants, whereas in some conventional protocol development processes, only a small number of participants provide their opinion on any given protocol. In some conventional approaches, the limited number of participants often requires additional time to develop adequate protocols for human phase trials. Some conventional approaches also require expert review of any given protocol and multiple reformulations of the protocol during development and even during the execution of a trial. Other conventional approaches limit the development process to the same participants, and fail to open development to a broader community.

According to some aspects, identification of known issues based on previous trials and the collective experience of the users becomes readily available during protocol development as a result of the curated environment. This open design approach can take advantage of the wisdom of the crowd by opening the protocol development process to a broad community. In some embodiments, the curated environment includes open development models, where protocol development questions are presented and results shared to facilitate protocol development. As a result, the protocols are developed faster and with a greater degree of certainty. In the curated environment, the development process insures that the appropriate questions have been identified, known issues have been explored, and the various inclusion/exclusion criteria for a given protocol have been evaluated to reduce any mistakes and/or changes in the protocol after a trial begins.

In some aspects, clinical study protocol development projects are curated by a scientific or patient review advocate. The scientific or patient review advocate interactively monitors the curated environment and publishes a partial list of scientific or patient-focused procedural issues/questions within the curated environment in a post related to a given clinical project for users to submit opinions and/or feedback. The problem(s) for which solutions are sought are referred to as protocol challenges. Each clinical study protocol can be organized based on subject matter, area of expertise (e.g., cardiology, neurology, infectious disease, etc.) of the protocol. A plurality of clinical study protocols can be designated by title within any subject matter category. The titles of each protocol can be reflective of the subject matter and provide additional description of the respective clinical study protocol. The environment can also be configured to provide access to protocol challenges based on the nature of the challenge for which a solution and/or participation is requested.

Compensation for submissions is determined based on an evaluation of the submissions received for a clinical study protocol. Review criteria are typically published with the protocol challenge. Acceptance of terms and the review criteria can be required prior to participation. In some embodiments, the research or patient advocates determine how well a submission meets the challenge and/or challenge requirements. In some implementations, research or patient advocates consider each of a set of review criteria, as discussed further herein, in the determination of scientific and technical merit, and give a separate score for each of the criteria for any submission provided by a user.

In some embodiments, the definition of a clinical study protocol includes a challenge to the participants to resolve issues associated with a drug protocol or provide information for improving a specific drug protocol. A given challenge can include review criteria for scoring any submission. A user submission does not need to be strong in all categories in any set of review criteria to be judged likely to have affected a success of a downstream clinical development project and earn awards. For example, a given development project may by its nature involve challenges with solutions that are not innovative. "Noninnovative" solutions may be essential to advance a clinical development project and thus earn compensation regardless of their novelty.

The protocol builder system can be configured to assign a research or patient advocate to each protocol challenge. The research or patient advocate evaluates each user submission. In some settings, each submission receives a score for each one of a set of review criteria, with submissions having higher scores earning compensation. In some embodiments, a research or patient advocate manually scores the submissions. In some embodiments, the research or patient advocate can employ discretion in weighing different criteria differently in developing an overall score for a given submission. Other embodiments can include evaluation components, which automatically review submissions for required criteria. Evaluation components can also be configured to provide suggested scores for review by a research or patient advocate. In some examples, natural language processing can be implemented on the evaluation components to identify a minimum level of compliance with the review criteria. In some other embodiments, the evaluation components can also be configured with learning algorithms to determine suggestions for scoring a given review criteria and/or generating an overall score for a submission. Once scoring is resolved, compensation can be determined according to any rules published for the protocol challenge.

According to another aspect, the system provides for peer review of user submissions. In some embodiments, peer review can influence protocol development, challenge selection, and/or quality evaluations associated with any user submission. In further embodiments, peer review can be used to determine compensation for participants, and in others, can be used as a factor in any compensation determination.

According to one aspect, a system for open clinical study protocol development is provided. The system comprises at least one processor operatively connected to a memory, the at least one processor when executing provides a user interface configured to register a plurality of users for access to a curated environment, wherein the user interface is further configured to provide access to protocol development projects, a challenge generation component configured to identify candidate challenges for protocol development, wherein each candidate challenge is configured to define at least one aspect of a clinical trial for a drug, an evaluation component configured to present candidate challenges for acceptance, wherein the evaluation component is further configured to receive approval for at least some of the candidate challenges, wherein the user interface is further configured to accept a plurality of submissions from a plurality of registered users in response to the approved challenges, and wherein the evaluation component is further configured to present the plurality of submissions for review by a review advocate.

According to one embodiment, the system further comprises matching component configured to match information in a protocol development project against existing clinical protocol approaches. According to one embodiment, the challenge generation component is configured to identify at least one candidate challenge for protocol development, responsive to the match by the matching component. According to one embodiment, the system further comprises a matching component is further configured to match a research or patient advocate to a protocol development project. According to one embodiment, the evaluation component is configured to present the candidate challenges to the research or patient advocate for approval. According to one embodiment, the evaluation component is further configured to receive scores for each of the plurality of submission from the research or patient advocate.

According to one embodiment, the system further comprises a communication component configured to deliver the plurality of submissions to each one of the plurality of registered users who submitted a response. According to one embodiment, the communication component is configured to provide access to protocol development projects and the plurality of submissions to any registered user. According to one embodiment, the communication component is configured to query publically available information on known protocol development approaches and define a template library of information associated with the known protocol development approaches. According to one embodiment, the evaluation component is configured to determine procedural and safety issues for at least one protocol development project. According to one embodiment, the evaluation component is configured to generate verifiable targets for inclusion in at least one protocol development project.

According to one embodiment, the challenge generation component is configured to define survey questions for at least one candidate challenge that define the at least one aspect of the clinical trial for the drug. According to one embodiment, the challenge generation component is configured to tailor survey questions to target at least one of: ideas from related publications, examples from similar projects, previously executed studies, and study population characteristics.

According to one aspect, a computer implemented method for clinical study protocol development is provided. The method comprises providing access to a user interface accessible over a communication network, displaying in the user interface a plurality of protocol development projects, accepting, by a computer system, a plurality of user submissions responsive to displayed challenges representing certain design elements associated with the protocol development projects, accepting, by the computer system, evaluations of the plurality of user submissions determined by a research or patient advocate, and establishing, by the computer system, at least one element of a clinical study protocol based on the evaluations of the plurality of user submissions.

According to one embodiment, the method further comprises an act of presenting the evaluations of the plurality of user submissions to a plurality of users, wherein the plurality of users input respective submissions for a respective protocol development project. According to one embodiment, the method further comprises an act of identifying, by the computer system, candidate challenges for protocol development, wherein each candidate challenge is configured to define at least one aspect of a clinical trial for a drug. According to one embodiment, the act of identifying includes an act of generating, by the computer system, at least one candidate challenge for protocol development, in response to matching at least one of the plurality of protocol development projects to an existing clinical protocol.

According to one embodiment, the method further comprises an act of presenting in a user interface candidate challenges for acceptance. According to one embodiment, the method further comprises an act of identifying potential users based on matches determined between information associated with a protocol development project and demographic information of the potential users. According to one embodiment, the method further comprises an act of inviting the potential users to participate in the protocol development project. According to one embodiment, the method further comprises an act of displaying the plurality of user submissions to registered users. According to one embodiment, the method further comprises an act of querying publically available information on known protocol development to define a template library of information associated with the known protocol development approaches. According to one embodiment, the method further comprises an act of determining, by the computer system, procedural and safety issues for at least one protocol development project.

According to one embodiment, the method further comprises an act of generating, by the computer system, verifiable targets for inclusion in the at least one protocol development project. According to one embodiment, the method further comprises an act of generating, by the computer system, survey questions for at least one of the displayed challenges, wherein the response are configured to define the at least one element of a clinical study protocol. According to one embodiment, the act of generating includes tailoring survey questions to target at least one of: ideas from related publications, examples from similar projects, previously executed studies, and study population characteristics. According to one embodiment, the plurality of user submissions include at least one of protocol challenges and responsive submissions.

According to another aspect, provided is a computer-readable medium having computer-readable signals stored thereon that define instructions that, as a result of being executed by a computer, instruct the computer to perform the method for clinical study protocol development. Various embodiments of the computer-readable medium implement the individual method steps above and their combination.

Other aspects, embodiments and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Any embodiment disclosed herein may be combined with any other embodiment. References to "an embodiment," "an example," "some embodiments," "some examples," "an alternate embodiment," "various embodiments," "one embodiment," "at least one embodiment," "this and other embodiments" or the like are not necessarily mutually exclusive and are intended to indicate that a particular feature, structure, or characteristic described in connection with the embodiment may be included in at least one embodiment. The appearances of such terms herein are not necessarily all referring to the same embodiment or example.

BRIEF DESCRIPTION OF THE DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

FIG. 11 is an example of a screen capture of an example user interface, according to one embodiment;

FIG. 12 is an example registration screen of a user interface, according to one embodiment;

FIG. 13 is a screen capture of an example protocol development project detail screen, according to one embodiment;

FIG. 14 is a screen capture of an example challenge screen, according to one embodiment;

FIG. 15 illustrates a screen capture of user interface showing challenge questions, according to one embodiment;

DETAILED DESCRIPTION

Figure 1:
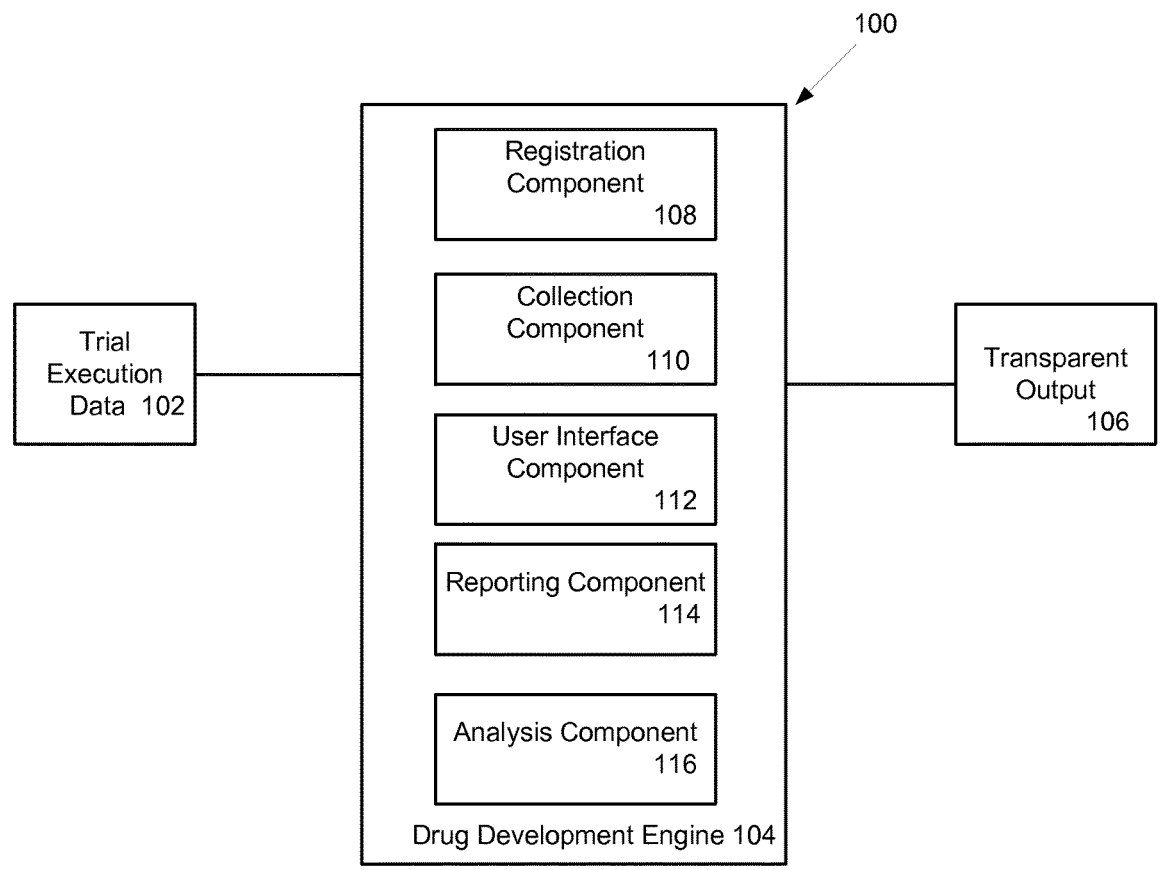
FIG. 1 is a block diagram of an example drug development system, according to one embodiment.

Several example features and additional embodiments describe approaches for crowd sourcing clinical drug development and/or execution using a transparent model for exposing information on all aspects of the development process. In some embodiments, various system components incorporate and/or are implemented in conjunction with the various embodiments, functions, methods, and operations discussed in co-pending U.S. patent application Ser. No. 13/679,242 and corresponding PCT Application PCT/US12/65514, titled SYSTEMS AND METHODS FOR CLINICAL PROTOCOL DEVELOPMENT," filed Nov. 16, 2012, which claim priority to U.S. Provisional Application No. 61/561,445, filed on Nov. 18, 2011, titled "SYSTEMS AND METHODS FOR CLINICAL PROTOCOL DEVELOPMENT," each of which are incorporated herein by reference in their entirety. In some embodiments, a drug development system is configured to provide interface elements that can be used to implement a web-based platform and incorporate one or more functions and/or methods of crowd sourcing, information presentation, as well as functions and/or methods of capturing, organizing, and analyzing data as further described below.

According to some aspects, provided are drug development systems configured to deliver drug development information transparently to registered participants. According to some embodiments, the drug development system can be configured to provide crowd source methodologies. In some embodiments, crowd sourcing methods of collecting, collating, and selecting ideas of designing drug development plans via a web-based platform, including but not limited to clinical study protocols, such as protocol builders are implemented on drug development systems. In further embodiments, a transparent method of presenting prior and recently acquired knowledge associated with a generic or a proprietary new chemical entity compound utilizing the web-based platform is implemented on drug development systems. In some embodiments, execution data (e.g., patient reported outcomes, automated health monitoring information, etc.) can be captured in real-time and presented on the system to registered users (e.g., physicians, clinicians, researchers, patients, etc.)

According to some embodiments, the implemented methods include sharing the acquired knowledge openly with Internet users willing to contribute to the design of drug development plans and/or clinical studies. In one embodiment, maintaining full data transparency helps stakeholders, including researchers, physicians, and patients, to compare results for trials performed using the web-based platform with published trials.

According to other embodiments, methods of capturing, organizing, and analyzing data from patients participating in clinical studies in real time are implemented on drug development systems. The methods can utilize telemedicine based approaches of data capture, and can further utilize methods of visualizing the captured data in real time on a web-based platform.

Shown in FIG. 1 is an example drug development system 100. The drug development system 100 can be configured to manage transparent drug development, for example, using a drug development engine 104. Elements of the system 100 can be provided using a computing system such as the computer system 300 and/or 302 described with reference to FIG. 3. For example, the development engine 104 can be executed on the computer system 300 and/or 302 to provide the functions and operations discussed herein. In other embodiments, the development engine 104 can include additional components executed on the computer system to perform specific operations. In some implementations, the system 100 and/or development engine 104 can be configured to communicate with protocol builder systems and/or integrate transparent drug development operations with combinations of the functions and system components of embodiments of the protocol builder system to manage transparent drug development.

As shown in FIG. 1, the system 100 and/or the development engine 104 is configured to receive trial execution data 102. According to some embodiments, trial execution data can include any remote data, for example, sleep monitoring data, patient-recorded outcome data, device reported data (e.g., blood pressure, pulse, heart rate, blood glucose level, analyte levels, walking speed, weight, activity levels, number of paces/strides, EKG data, etc.). Various remote monitoring devices can incorporate communication components configured to report, automatically, monitored information to the development engine 104 and/or system 100. According to various embodiments, the development engine 104 can be configured to process trial execution data 102 to generate and/or display a transparent output 106 from a trial execution.

In one embodiment, transparent output 106 can include the raw trial execution data 102 presented to registered users accessing system 100 and/or development engine 104. In other embodiments, the raw data can be aggregated and/or analyzed to provide summary views of the raw trial execution data. In further embodiments, raw and summary data is generated for viewing by registered users such that patient identity is anonymized (e.g., as transparent output 106). The transparent output 106 is generated by the system 100 and/or development engine 104 according to an open data model. The open data model can be designed to provide transparent access to trial execution information to all participants (e.g., researches, trial patients, and outside observers) so that the broader user community can benefit from a protocol development project and learn from information captured during execution.

Varying configurations of the open or transparent data model can be defined to implement transparent development and/or execution. In some embodiments, the open data model and transparent development can be configured to provide access to protocol building functions and operations as well as trial execution data to all registered users. In other embodiments, the open data model can be configured to limit access to registered users who have agreed to restrictions specified for the system, or for specific protocol building and/or execution projects. For example, registered users can be required to hold any data accessed on the system in confidence (e.g., users must agree to a non-disclosure agreement as part of registration). In some embodiments, different levels of access to information can be implemented through the open data model. In some embodiments, different levels of access can be implemented on the system responsive to user type (e.g., patient, researcher, observer, clinician, physician, etc.).

In further embodiments, the open data model can be configured to deliver whatever information that can be delivered to the registered user population while not violating any agreements or requirements. For example, FDA trial requirements can dictate that specific trial information not be shared with participants or observers of an ongoing trial. FDA requirements may provide restrictions on the sharing of information more generally, and the open data model can be configured to respect those requirements.

In other embodiments, the open data model can be specially configured to a client wishing to develop and/or execute a clinical protocol. For example, the client may wish to tap crowd-sourced information but preserve confidentiality and/or dictate some constraints on publication of protocol and/or execution information (e.g., within the system). In some embodiments, the open data model can be configured to meet the requirements of one or more clients. According to one embodiment, different trials can also include different restrictions specified by the open data model. For example, patient information can be treated, analyzed, and/or provided differently relative to other trials based on restrictions defined in the open data model for respective trials.

According to some embodiments, the development engine 104 and/or system 100 is configured to published execution data including, for example, patient data. In one embodiment, development engine 104 and/or system 100 is configured to match user captured data with other patient data to provide, for example, learning opportunities. In some embodiments, the development engine 104 matches current patient records to prior clinical study data to provide context for understanding their own experience. In one example, the transparent data model implemented by the development engine 104 can be configured to teach a clinical trial patient how to compare their information to other trial patients and/or trial participants from previously executed trials. According to some embodiments, visualizations of trial execution data can be tailored to a specific patient (e.g., a current user). For example, the patient can be presented a view by the development engine 104 of their own data in the context of other trial participants' data. In another example, the patient can be presented a view by the system of their own data in the context of other drug trial executions.

In further embodiments, the clinical trial patients can also be provided a communication link with the clinical trial investigator or manager through the drug development system. Through open two-way communication, the clinical trial patients can be more actively involved in development of a trial protocol and during the execution of the trial protocol. Further, open communication with the clinical trial investigators enables better understanding of the patient's position in the trial (e.g., outcome analysis, even outcome projections, education on the patient's data, etc.). In some embodiments, patients can be educated on the placebo effect (an apparent benefit derived by patients not receiving the trial medication) and have a vehicle for learning more from the trial investigators.

In some embodiments, patient questions can be published to the development community at large. In some examples, participant published data can be vetted by curators, prior to publication to the open community. In further embodiments, curators can review public postings by registered users.

According to some embodiments, the development engine 104 can include various components configured to perform specialized operations in association with the drug development system 100. In other embodiments, the development engine 104 can be configured to perform the specialized operations more generically under the control of the development engine 104 directly, rather than requiring specific components.

According to some embodiments, the development engine 104 can include a registration component 108. The registration component 108 can be configured to provide functions through a web-based user interface. In some embodiments, the registration component can be configured to accept registration information on trial candidates. In other embodiments, the registration component 108 can be configured to solicit registrations from patient information that suggest candidates who may be suitable to participate in a particular study.

In some embodiments, the registration component 108 can be configured to establish user accounts and access credentials. The accounts and features provided can be specific to the user being registered. In one example, clinical patient accounts can be configured to associate clinical execution information with registered patients. In further embodiments, the registration component 108 can be configured to manage informed consent for trial participants and store associated documentation for each patient/participant for access by the development engine 104 and/or system 100. The development engine 104 can also be configured to provide access to execution information to registered patients on a patient by patient basis. As discussed, individual patients can access their information directly, and further access their information in the context of other participants and/or prior trial executions.

In some embodiments, the development engine 104 can include a collection component 110 configured to capture trial execution information in real-time or near real-time. According to one embodiment, the collection component 110 can be configured to receive monitoring information from health monitoring devices provided to registered participants. The monitoring devices can include, for example, automated medicine delivery devices. In one example, devices with medication trays that contain multiple medication compartments (e.g., 30-48), an electronic timer/alarm, and electronic monitoring systems can be provided to registered participants in conjunction with trial executions.

The drug delivery devices can be configured to alert patients when it is time to take study medication, and further to record each time a patient accesses a compartment. The drug delivery devices can be configured to upload drug delivery data (e.g., daily, hourly, periodically, on a schedule, etc.) to the drug development system (including failures to access a required compartment or accessing excess compartments). The drug delivery data can be stored in data records associated with each patient. In one embodiment, the delivery data can be saved in a repository on the drug development system 100 (e.g., a database or other data repository).

According to some embodiments, the collection component 110 can also be configured to communicate with health monitoring devices for participants in clinical trials. In some examples, the health monitoring devices can capture data actively and passively. In further examples, the health monitoring devices can include telemonitoring of data that are actively captured by an electronic device as follows: data are collected directly by a monitoring device (e.g., automated blood pressure (BP) cuff); data collection can be actively initiated by the subject (e.g., subject puts on and activates automated BP cuff); the device automatically connects (e.g., via Bluetooth) to a modem (e.g., landline, cellular, cable), and then uploads data to, for example, a database.

In further examples, the health monitoring devices can include telemonitoring of data that is passively captured by an electronic device, as follows: data such as activity details (e.g., steps, distance, overall activity, gait, sit-to-stand transfer, postural sway, falls, etc.); medication dispensing/compliance information (e.g., each time study medication is accessed by the subject); activity information provided by use of a smartphone, tablet, accelerometer/actigraph can also be collected; and electronic medication dispenser/reminder/compliance monitor information can also be collected. According to some embodiments, passive data collection can be initiated by the subject (e.g., while the subject wears an accelerometer or when they use the medication dispenser, the device automatically collects the data, in other examples computing devices including GPS or other tracking systems can also be used to passively monitor patient activity).

According to one embodiment, the clinical trial investigator can review such electronic data (e.g., after being alerted via SMS text, by logging in to a web portal, etc.), and follow up with the subject and/or take action/implement care as necessary (e.g., sees a safety concern and asks the subject to come in for an unscheduled visit), and further the system 100 provides for the investigator to document his/her follow-up on the system 100.

In some embodiments, the system 100 can include a user interface component 112 to provide for communication between trial participants and the system 100. In further embodiments, the UI component 112 can be further configured to provide Interactive Voice/Web/Voice and Video Response (IVR/IWR/IVVR) systems to enable direct communication between clinical trial participants and trial investigators. In some embodiments, the system enables bi-directional video and audio that includes interaction with and/or observation by a clinician through the UI component 112.

In addition, the system 100 can provide secure web pages that allow registered patients to enter and view their data, and receive instructions from trial investigators or clinicians. According to some embodiments, the system 100 can include telecommunications devices for collection and reporting (e.g., telephone, SMS text, touch tone questionnaire, etc.).

According to one embodiment, the development engine 104 can include a reporting component 114 configured to present trial execution data (e.g., data collected from drug delivery devices, health monitoring devices, and patient input) through, for example, the UI component 112. In some embodiments, the reporting component 114 can generate user interface displays and associated data for presentation by the UI component 112. As discussed, registered patients are able to view their own data. In addition, other registered users are also able to view trial execution data as that data is collected. In one example, the reporting component 114 publishes information on real-time data, which can include aggregated information and/or can include raw information received by the collection component 110.

In some embodiments, the development engine 104 includes an analysis component 116 configured to process raw data collected from groups of patients into summary information published to the community of registered users (e.g., physicians, clinicians, patients, etc). The analysis component 116 can also be configured to match current trials to prior studies. In some examples, the analysis component 116 can be configured to capture publically available clinical study information and provide the information to match against ongoing trials. Further, prior trial executions on the system 100 and the associated information collected for each trial can be analyzed by the analysis component 116 to provide matching information to current trial patients, trial investigators, and any registered users. The current execution information can be used by the analysis component 116 to generate predictions regarding patient outcomes, clinical end-point targets (e.g., futility in continued execution, a degree of confidence in meeting end-point, etc.), and in some embodiments to refine or re-configure trial end-points.

In some embodiments, the analysis component 116 is configured to aggregate execution data and publish the aggregated information for review by the registered users of the system 100. Publishing the execution data during the actual execution of the trial (e.g., as transparent output 106) provides unique opportunities to refine, augment, or even terminate a clinical trial early. In some examples, the registered users can provide insight into the published execution data that provides for better planning of subsequent trials. In other examples, the registered users can provide insight in altering trial end-points. Altering trial end-points can include, for example, reducing procedures executed on the clinical trial population, or altering a dosing regimen based on real-time data capture.

In some embodiments, the analysis component 116 can be configured to facilitate trial planning using Bayesian or other probabilistic modeling approaches. Trial planning generated by the analysis component 116 can be provided to a protocol builder system or system components that can be used to analyze and/or refine such planning models.

In further embodiments, the analysis component 116 can be configured to provide comparison tools, for example, in conjunction with the UI component 112. The comparison tools can be configured to enable a user to view execution data, subsets of execution data, visualize current patient execution data against subsets within the execution data, visualize execution data within groups of patients (e.g., placebo, dosing regimen A, dosing regimen B), visualize execution data between subsets within the execution data, and/or visualize current execution data against other trial executions or published trial information.

In some examples, the comparison tools are configured to accept user specification of filter criteria to define subsets within any execution data being viewed. In some settings, the system defaults to execution information for a current trial associated with a user's account. The comparison tools can provide options for selecting or filtering execution data, for example, by patient, patient demographic information (height, weight, symptoms, treatment results, sex, age, etc.). Any filtered or selected group within the execution data can be compared via selection in the comparison tools. For example, a user can specify a comparison group by selecting within the execution data to define the comparison group for display.

In further embodiments, the system can be configured to provide matching information for registered trial patients.

The system can also be configured to provide the matching trial execution information (e.g., identified by the analysis component) with identification of the criteria that generated the matches. The criteria can be provided by the system as selections within visual displays to allow a user to further define or select within the matching information.

According to some embodiments, the system 100 and/or development engine 104 can accept user input to generate various examples of transparent outputs 106. In some implementations, the system can provide transparent outputs 106 in conjunction with protocol builder systems. In one embodiment, a drug development system can provide a platform for registering users, tracking and publishing clinical trial execution data, for example, as a transparent output 106.

Various embodiments of the system for drug development can implement crowd sourcing methods of collecting, collating, and selecting ideas of designing drug development plans via a web-based platform, including but not limited to clinical study protocols, such as protocol builders. The crowd sourcing methods can cover all stages of the drug development cycle including pre-clinical (pre-IND), early stages of clinical development (phase 1/2a), mid and late stages of clinical development (phase 2b/3), and post marketing approval stages (phase 4).

Some examples of crowd sourcing methods include crowd-sourced design of clinical protocols for both repurposed generics and new chemical entities (NCEs) in a wide variety of disease indications. In one embodiment, crowd-sourced design methods are applied to repurposed generics and NCEs in chronic diseases such as multiple sclerosis, inflammatory bowel disease, and peripheral vascular disease. For these example indications, use of a web-based protocol building approach can elicit crowd input. The crowd input can include, but is not limited to, clinical endpoints, inclusion/exclusion criteria, dosing, and data analysis. In one embodiment, a secondary endpoint in an indication, such as multiple sclerosis, may be amenable to use of remote data collection techniques, such as sleep monitoring or patient-recorded outcomes, which may reduce costs and increase utility for that endpoint.

Figure 2:
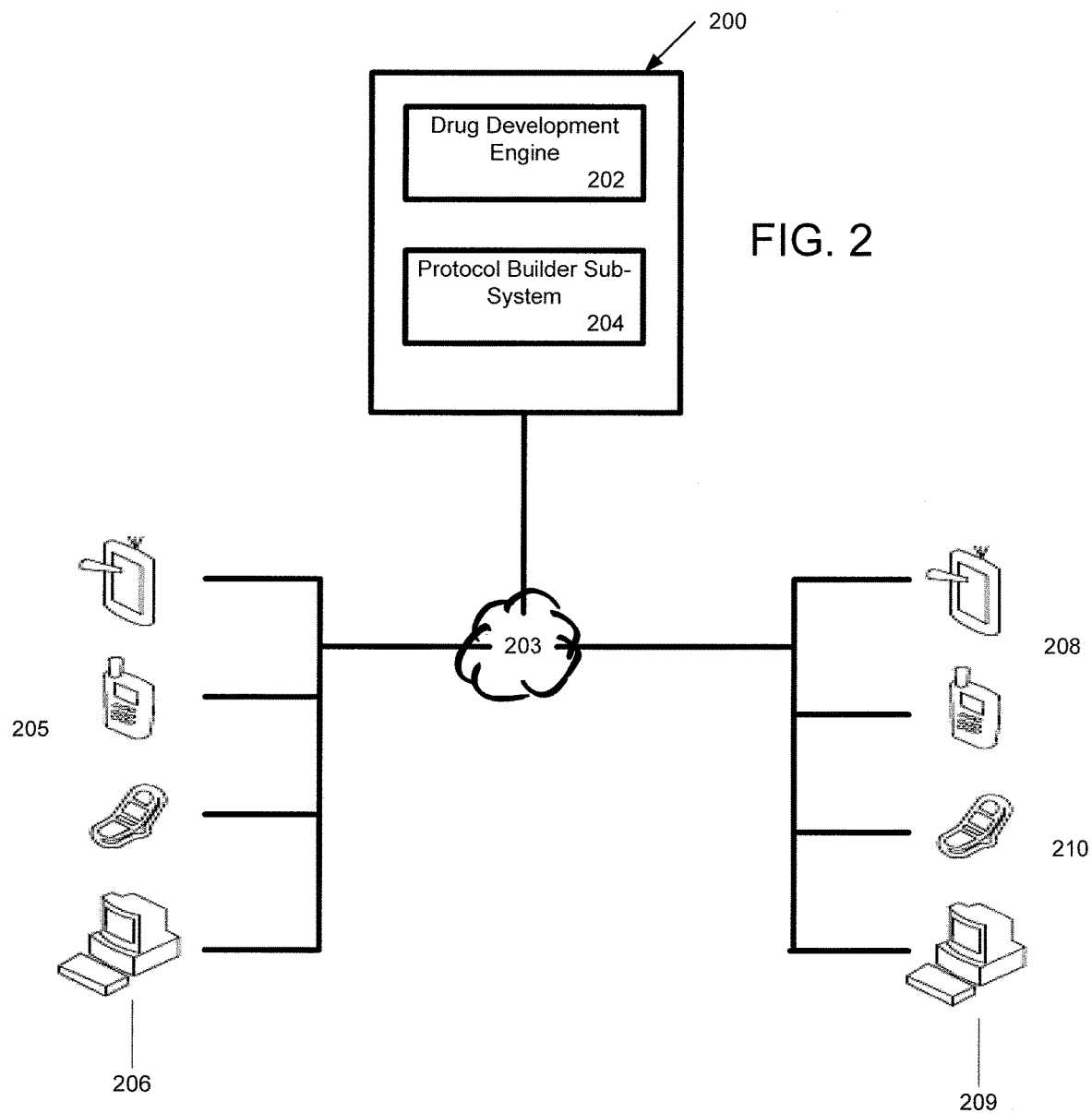
FIG. 2 is a block diagram of an example drug development system, according to one embodiment

In further embodiments, the system implements a transparent method of presenting prior and recently acquired knowledge associated with a generic or a proprietary new chemical entity compound utilizing the web-based platform. Shown in FIG. 2 is an example drug development system 200. The drug development system can include a drug development engine 202 implementing one or more of the functions described above. The drug development system can also include a protocol builder subsystem 204 that implements one or more of the functions discussed herein with respect to protocol builder systems. The drug development system 200 can be accessed by trial participant 206 over a communication network 203. The communication network can include any one or more of known communication networks LAN, WAN, MAN and can include, for example, the Internet. The trial participants 206 can access the drug development system through their computing devices 205 (e.g., computing devices 205 can include laptops, desktops, mobile computing systems, smart-phones, PDAs, etc.). In some examples, the computing devices 205 can include medicine delivery systems and/or health monitoring devices that can report to the drug development system automatically.

Information communicated to the drug development system 200 can be reviewed and analyzed by the trial investigators 208 via their computing devices 209 (e.g., computing devices 209 can include laptops, desktops, mobile computing systems, smart-phones, PDAs, etc.). In some embodiments, trial execution data collected by the drug development system can also be provided to other registered users of the drug development system 200. For example, other participants 210 (including e.g., other trial patients, other trial investigators, physicians, clinicians, statisticians, etc.) can access collected trial execution data to provide their analysis and/or input. As discussed, the system can implement a transparent data model, where trial execution data is communicated to all participants who wish to be involved in the drug development process.

According to some embodiments, the transparent methods executed by the system can include sharing the acquired knowledge openly with Internet users willing to contribute to design of drug development plans and/or clinical studies. In one embodiment, maintaining full data transparency helps stakeholders, including researchers, physicians, and patients, to compare results for trials performed using the web-based platform with published trials. Such a comparison can help to assess utility of trial parameters including endpoints, inclusion/exclusion criteria, and dosing. In another embodiment, data transparency may facilitate design of novel trial methods, including but not limited to, adaptive/Bayesian designs. In still another embodiment, availability of aggregated real-time trial data may elicit commentary from statisticians as to the expected outcome of a trial. This may improve the ability to make decisions regarding duration of the study. For example, decisions can include terminating trials for futility, thereby potentially avoiding unnecessary exposure of patients to study medication, and reducing expense.

In other embodiments, the system can be configured to execute methods of capturing, organizing, and analyzing data from patients participating in clinical studies in real time. The method, in one example, may utilize telemedicine based methods of data capture, and may further utilize methods of visualizing the captured data in a real time on the web-based platform. In another example, the method can include subjecting the captured data to crowd-based scrutiny. In one embodiment, remote monitoring techniques include, but are not limited to, direct patient data collection for parameters such as blood pressure, pulse, heart rate, blood glucose level, analyte levels, walking speed, and weight. In another embodiment, the system can execute processes to collect data using remote patient-reported outcome (PRO) approaches. In another embodiment, clinical studies can be designed with primary and/or secondary endpoints built around continuous measurements facilitated by telemedicine.

Figure 3:
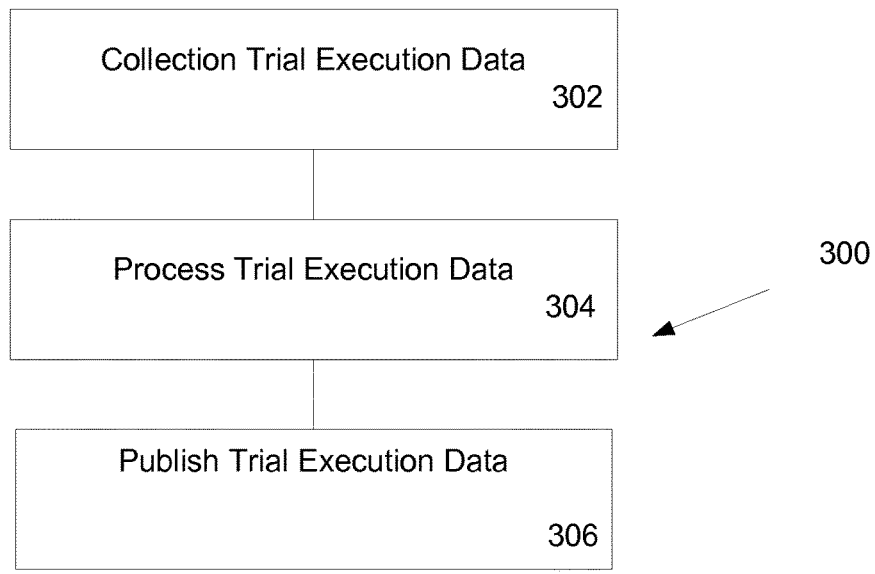
FIG. 3 is an example process flow for receiving and processing trial execution data within a transparent development model, according to one embodiment.

Shown in FIG. 3 is an example process 300 for collecting and publishing trial execution data. The process 300 begins at 302 with collection of trial execution data. According to some embodiments, step 302 can be executed by receiving health information from monitoring devices provided to trial patient populations. In some embodiments, the patient populations can first be registered for participation, and monitoring devices delivered to the registered participants configured for respective trials. In one example, the patient population can register to participate through a drug development system, and the system can manage delivery of monitoring devices to each patient. At 302, the trial execution data is collected from the monitoring devices. Additionally, data may be captured directly from patients.

In some embodiments, the devices are configured to communicate respective data automatically. For example, the devices can include medicine tracking systems. The medicine tracking systems can be configured to provide notices to respective patients to take their medication according to the clinical trial parameters. The medicine tracking systems can track access by a respective patient to their trial medicine. The system accesses information to insure compliance by respective patients.

In other embodiments, monitoring devices can be triggered to communicate information in response to user direction. For example, registration on the system can include delivery of a software-based application to a patient's computing device. In some embodiments, the delivered application can be configured to employ available sensors on the patient's computing device to capture and transmit health information. In one example, sensors available on the computing device can be used to track the patient's activity level. Accelerometers or GPS sensors can provide information on patient activity (walking, strides, etc.). In some embodiments, the patient may need to activate the application in order for it to track patient activity and/or communicate activity information for collection at 302.

At 304, trial execution data can be processed. The processed trial execution data can be published at 306, for example, to trial investigators or other interested parties. In some embodiments, processing at 304 includes anonymizing the execution data to remove patient identifying information. In other embodiments, processing at 304 can include aggregating the trial execution data to provide summary information. The summary information can include, for example, statistical aggregations of patients' responses. The statistical aggregations can include patient reported outcome information, health information received from monitoring devices (e.g., blood pressure, pulse, heart rate, blood glucose level, analyte levels, walking speed, weight, activity levels, number of paces/strides, EKG data, etc.), aggregations of data collected by end-point or test criteria, among other options.

In some embodiments, processing of execution data at 304 can include aggregations of trial execution data for comparison to other patients, comparison to other trials, and/or comparison to information on published trials. For example, processing can include generation of displays for visually comparing trial execution data and the visual displays can be published at 306. In some embodiments, processing of the execution data at 304 can include associating execution data with a specific patient from the patient population. For example, the execution data can be stored in data records specified by a patient identifier. In some examples, the patient identifier can be generated or assigned to insure the anonymity of the patient and/or execution data. According to one embodiment, the patient identifier can be assigned as part of a registration process for a clinical trial.

According to some embodiments, process 300 can be executed as one of a number of processes for collecting and publishing trial execution information. In some embodiments, process 300 can be executed by a drug development engine (e.g., 104 and 202) and/or drug development system (e.g., 100 and 200). The development engine and/or system can also execute other processes in conjunction with 300, for example, to provide the functions discussed herein.

Figure 4:
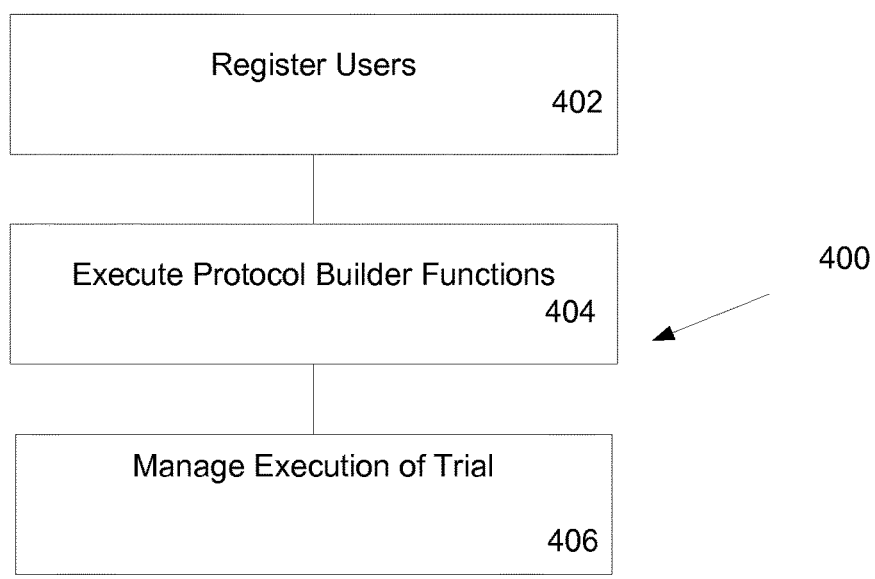
FIG. 4 is an example process flow for receiving and processing trial execution data within a transparent development model, according to one embodiment

Shown in FIG. 4, is an example process 400 for generating and managing clinical trial execution. Process 400 begins at 402 with registration of users, who wish to participate in development of a clinical trial protocol. At 402, trial investigators can register and be provided access to a protocol builder environment. Other users can register at 402 as well. For example, patients can register and participate in developing a clinical trial protocol. According to some embodiments, registration at 402 includes specification of access credentials (e.g., user name and password) for a protocol builder platform. The protocol builder platform can be configured to allow any interested party to register as a user (e.g., patients, trial investigators, physicians, clinicians, technicians, etc.). In some examples, anyone wishing to contributed can be registered and provide their opinion and/or suggestions regarding development of a clinical trial protocol.

At 404, protocol building functions are executed to define aspects of a clinical trial protocol. The clinical trial protocol can include publication of candidate test options (e.g., clinical end-points) for determining final tests to be included in a trial protocol. In some embodiments, the candidate test options can be commented on, voted for or against, by any registered users. Responsive to any one or more of commentary, voting, suggested alternatives etc, parameters for a clinical trial can be defined at 404.

In some implementations, step 404 can be executed repeatedly to define multiple parameters for the clinical trial. In other implementations, step 404 can be executed until the parameters for the clinical trial are defined for the clinical trial. In some embodiments, the process 400 can continue once the parameters for the clinical trial are defined at 406 with managing the execution of the defined parameters (including, for example, drugs to administer, clinical end-points to measure during the trial, testing to be performed, reporting criteria, patient interviews, etc.).

According to some embodiments, managing execution of the clinical trial parameters at 406 can include remotely monitoring a clinical trial patient population via telemedicine techniques. The definition of the clinical trial parameters at 404 can include testing criteria that can be measured remotely. In some embodiments, definition of clinical trial parameters at 404 can also be configured to recommend or favor selection of test criteria that can be implemented through remote monitoring devices.

In further embodiments, managing execution at 406 can include delivering automated medication delivery devices to the patient population for the clinical trial. Any automated trial execution information can be received as part of managing execution at 406. The trial execution information can be published to the registered users as part of execution of 406. In some embodiments, the trial execution information can be processed to remove any patient identifying information prior to publication.

According to some implementations, process 400 can be executed by a drug development engine (e.g., 104 and 202) and/or a drug development system (100 and 202) to provide for holistic drug protocol generation and execution. The holistic approach to drug protocol generation and execution can leverage the combined wisdom of the registered users of the system. By allowing registration of patients, investigators and other interested parties a transparent drug development process is implemented that facilitates quicker and more efficient generation of drug trials. Further by executing the trial transparently, the entire community's understanding is enriched, maximizing the benefit derived, even from failed clinical trials.

According to one embodiment, clinical trial investigators can register to generate a clinical trial protocol (e.g., at 404), receive input from other users registered at 402 as part of the generation of the clinical trial, and manage its execution at 406. The clinical trial investigators can, for example, deliver monitoring devices to a registered patient population and automatically receive remote trial execution data as part of 406. Further, the contributions of the registered users do not end with the generation of clinical trial protocol, rather, the insights and opinions on the execution of the clinical trial can provide additional efficiencies. For example, statistical analysis on the trial execution data can be submitted by any of the registered users to validate the clinical investigators conclusions. In other examples, statistical analysis by the registered users can provide indications that a particular trial, end-point, and/or parameter cannot be achieved or is futile. In such settings, the trial may be concluded early responsive to user analysis. In other executions, the trial, end-point, and/or parameter may be adapted responsive to the user analysis to provide for an augmented or altered end-point and/or parameter. Various embodiments of drug development systems can execute process 400 to leverage to the combined wisdom of the user population and provide for transparent protocol generation and execution.

Example Drug Development System Implementations

Various aspects and functions described herein in accord with the present invention may be implemented as hardware, software, or a combination of hardware and software on one or more computer systems. There are many examples of computer systems currently in use. Some examples include, among others, network appliances, personal computers, workstations, mainframes, networked clients, servers, media servers, application servers, database servers, web servers, health monitoring devices, drug delivery systems, and virtual servers. Other examples of computer systems may include mobile computing devices, such as cellular phones and personal digital assistants, and network equipment, such as load balancers, routers and switches. Additionally, aspects in accord with the present invention may be located on a single computer system or may be distributed among a plurality of computer systems connected to one or more communication networks.

For example, various aspects and functions may be distributed among one or more computer systems configured to provide a service to one or more client computers, or to perform an overall task as part of a distributed system. Additionally, aspects may be performed on a client-server or multi-tier system that includes components distributed among one or more server systems that perform various functions. Thus, the invention is not limited to executing on any particular system or group of systems. Further, aspects may be implemented in software, hardware or firmware, or any combination thereof. Thus, aspects in accord with the present invention may be implemented within methods, acts, systems, system placements and components using a variety of hardware and software configurations, and the invention is not limited to any particular distributed architecture, network, or communication protocol. Furthermore, aspects in accord with the present invention may be implemented as specially-programmed hardware and/or software.

Figure 5:
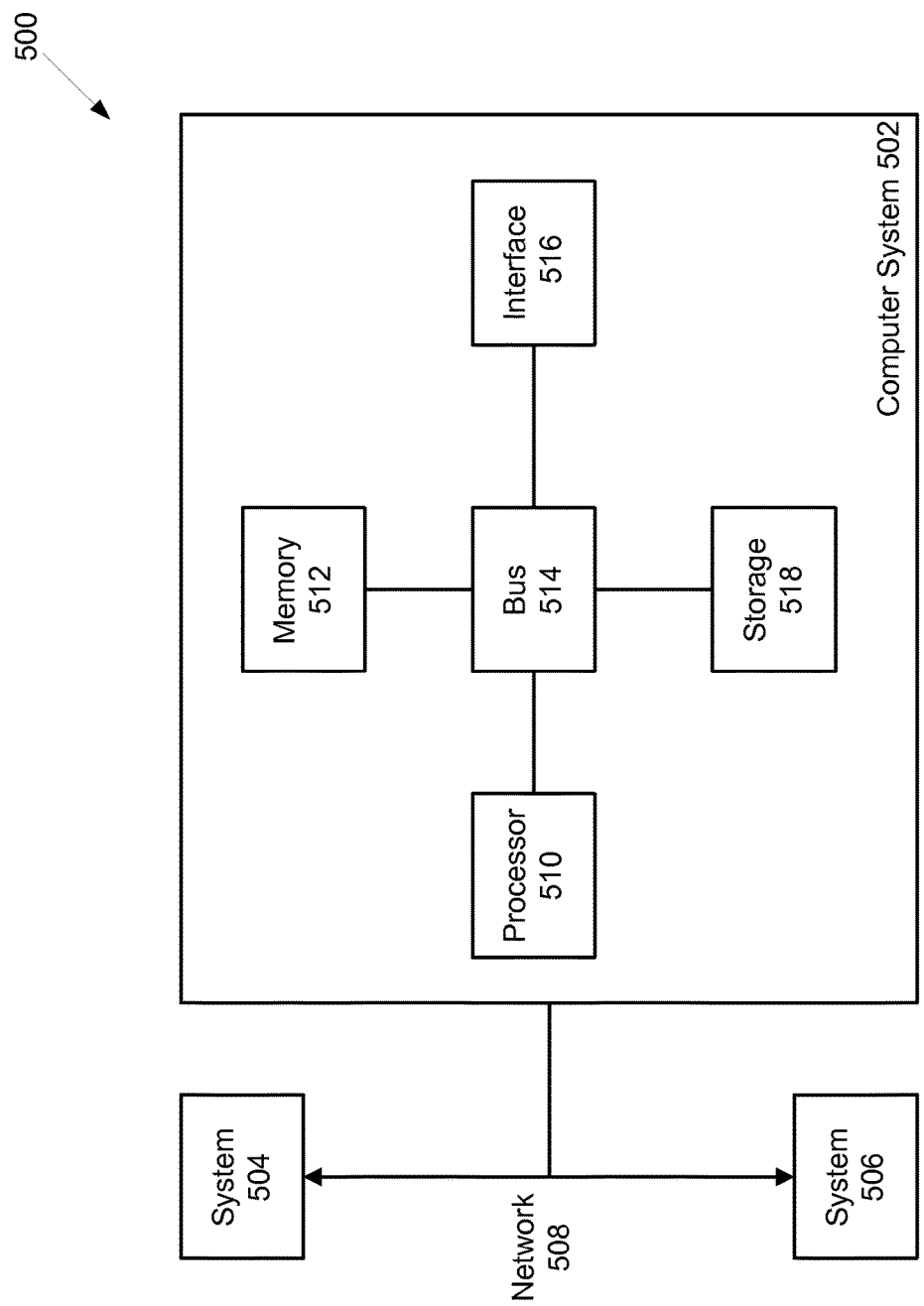
FIG. 5 is a block diagram of an example drug development system, according to one embodiment.

FIG. 5 shows a block diagram of a distributed computer system 500, in which various aspects and functions in accord with the present invention may be practiced. The distributed computer system 500 may include one or more computer systems. For example, as illustrated, the distributed computer system 500 includes three computer systems 502, 504 and 506. As shown, the computer systems 502, 504 and 506 are interconnected by, and may exchange data through, a communication network 508. The network 508 may include any communication network through which computer systems may exchange data. To exchange data via the network 508, the computer systems 502, 504 and 506 and the network 508 may use various methods, protocols and standards including, among others, token ring, Ethernet, Wireless Ethernet, Bluetooth, TCP/IP, UDP, HTTP, FTP, SNMP, SMS, MMS, SSB, JSON, XML, REST, SOAP, CORBA HOP, RMI, DCOM and Web Services. To ensure data transfer is secure, the computer systems 502, 504 and 506 may transmit data via the network 508 using a variety of security measures including TSL, SSL or VPN, among other security techniques. While the distributed computer system 500 illustrates three networked computer systems, the distributed computer system 500 may include any number of computer systems, networked using any medium and communication protocol.

Various aspects and functions in accordance with the present invention may be implemented as specialized hardware or software executing in one or more computer systems including the computer system 502 shown in FIG. 5. As depicted, the computer system 502 includes a processor 510, a memory 512, a bus 514, an interface 516 and a storage system 518. The processor 510, which may include one or more microprocessors or other types of controllers, can perform a series of instructions that manipulate data. The processor 510 may be a well-known, commercially available processor such as an Intel Pentium, Intel Atom, ARM Processor, Motorola PowerPC, SGI MIPS, Sun UltraSPARC, or Hewlett-Packard PA-RISC processor, or may be any other type of processor or controller as many other processors and controllers are available. As shown, the processor 510 is connected to other system placements, including a memory 512, by the bus 514.

The memory 512 may be used for storing programs and data during operation of the computer system 502. Thus, the memory 512 may be a relatively high performance, volatile, random access memory such as a dynamic random access memory (DRAM) or static memory (SRAM). However, the memory 512 may include any device for storing data, such as a disk drive or other non-volatile storage device, such as flash memory or phase-change memory (PCM). Various embodiments in accord with the present invention can organize the memory 512 into particularized and, in some cases, unique structures to perform the aspects and functions disclosed herein.

Components of the computer system 502 may be coupled by an interconnection element such as the bus 514. The bus 514 may include one or more physical busses (for example, busses between components that are integrated within a same machine), and may include any communication coupling between system placements including specialized or standard computing bus technologies such as IDE, SCSI, PCI and InfiniBand. Thus, the bus 514 enables communications (for example, data and instructions) to be exchanged between system components of the computer system 502.

Computer system 502 also includes one or more interface devices 516 such as input devices, output devices and combination input/output devices. The interface devices 516 may receive input, provide output, or both. For example, output devices may render information for external presentation. Input devices may accept information from external sources. Examples of interface devices include, among others, keyboards, mouse devices, trackballs, microphones, touch screens, printing devices, display screens, speakers, network interface cards, etc. The interface devices 516 allow the computer system 502 to exchange information and communicate with external entities, such as users and other systems.

Storage system 518 may include a computer-readable and computer-writeable nonvolatile storage medium in which instructions are stored that define a program to be executed by the processor. The storage system 518 also may include information that is recorded, on or in, the medium, and this information may be processed by the program. More specifically, the information may be stored in one or more data structures specifically configured to conserve storage space or increase data exchange performance. The instructions may be persistently stored as encoded signals, and the instructions may cause a processor to perform any of the functions described herein. A medium that can be used with various embodiments may include, for example, optical disk, magnetic disk or flash memory, among others. In operation, the processor 510 or some other controller may cause data to be read from the nonvolatile recording medium into another memory, such as the memory 512, that allows for faster access to the information by the processor 510 than does the storage medium included in the storage system 518. The memory may be located in the storage system 518 or in the memory 512. The processor 510 may manipulate the data within the memory 512, and then copy the data to the medium associated with the storage system 518 after processing is completed. A variety of components may manage data movement between the medium and the memory 512, and the invention is not limited thereto.

Further, the invention is not limited to a particular memory system or storage system. Although the computer system 502 is shown by way of example as one type of computer system upon which various aspects and functions in accord with the present invention may be practiced, aspects of the invention are not limited to being implemented on the computer system, shown in FIG. 5. Various aspects and functions in accord with the present invention may be practiced on one or more computers having different architectures or components than that shown in FIG. 5. For instance, the computer system 502 may include specially-programmed, special-purpose hardware, such as for example, an application-specific integrated circuit (ASIC) tailored to perform a particular operation disclosed herein. Another embodiment may perform the same function using several general-purpose computing devices running MAC OS System X with Motorola PowerPC processors and several specialized computing devices running proprietary hardware and operating systems.

The computer system 502 may include an operating system that manages at least a portion of the hardware placements included in computer system 502. A processor or controller, such as processor 510, may execute an operating system which may be, among others, a Windows-based operating system (for example, Windows NT, Windows 2000/ME, Windows XP, Windows 7 or 8, or Windows Vista) available from the Microsoft Corporation, a MAC OS System X operating system available from Apple Computer, one of many Linux-based operating system distributions (for example, the Enterprise Linux operating system available from Red Hat Inc.), a Solaris operating system available from Sun Microsystems, or a UNIX operating systems available from various sources. Many other operating systems may be used, and embodiments are not limited to any particular operating system.

The processor and operating system together define a computing platform for which application programs in high-level programming languages may be written. These component applications may be executable, intermediate (for example, C# or JAVA bytecode) or interpreted code which communicate over a communication network (for example, the Internet) using a communication protocol (for example, TCP/IP). Similarly, functions in accord with aspects of the present invention may be implemented using an object-oriented programming language, such as SmallTalk, JAVA, C++, Ada, or C# (C-Sharp). Other object-oriented programming languages may also be used. Alternatively, procedural, scripting, or logical programming languages may be used.

Additionally, various functions in accord with aspects of the present invention may be implemented in a non-programmed environment (for example, documents created in HTML, XML or other format that, when viewed in a window of a browser program, render aspects of a graphical-user interface or perform other functions). Further, various embodiments in accord with aspects of the present invention may be implemented as programmed or non-programmed placements, or any combination thereof. For example, a web page may be implemented using HTML while a data object called from within the web page may be written in C++. Thus, the invention is not limited to a specific programming language and any suitable programming language could also be used.

In addition, the method described herein may be incorporated into other hardware and/or software products, such as a website, a mobile device, drug delivery device, health monitoring device, or a navigation unit.

Example Protocol Builder System

One embodiment of a protocol builder system provides for interactive protocol design and analysis. The system provides users with a controlled, curated environment for clinical study protocol synthesis, formal analysis, and offers both software and hardware components configured for protocol assessment and optimization. The system assists the user in the documentation of clinical study protocol designs by autonomously extracting protocol templates based on analysis of the clinical study protocol submitted to the system. The system can be further configured for the generation of protocol implementations from abstract specifications that can be executed as part of a trial. The system can also be configured to prompt participants (e.g., researchers) to widen the scope of clinical study protocol reviews, opening project development to a broad community. The system can also be configured to permit all stakeholders in the project visibility into, and overall confidence in, the development of an on-going scientific project. In some implementations, the system provides for transparent development from multiple perspectives, including, for example, open development by a broad community, and also, provides visibility for stakeholders interested in the protocol development.

It is realized that when writing a clinical study protocol the scientist or the patient affected by disease to be researched in any given scientific experiment initially strives to clarify the reason behind the science, in other words, the structure and operational aspects of the project. According to some aspects, it is recognized that no one individual (or even one drug development group) has complete knowledge of every drug trial. The protocol builder system prompts stakeholders (e.g., researchers, physicians, patients, drug developers, etc.) for timely input on pivotal project challenges. According to some embodiments, decisions based upon research methods, clinical study population, statistical analysis, clinical study design, clinical study procedures, and potential adverse events are examined and cleared by a large population of users. As these decisions influence all of the downstream clinical trial costs and project completion dates, the protocol builder system reduces complexity, costs, and risks associated with developing and implementing clinical study protocols. In some examples, the protocol builder system can be configured specifically to facilitate drug protocol development.

Figure 6:
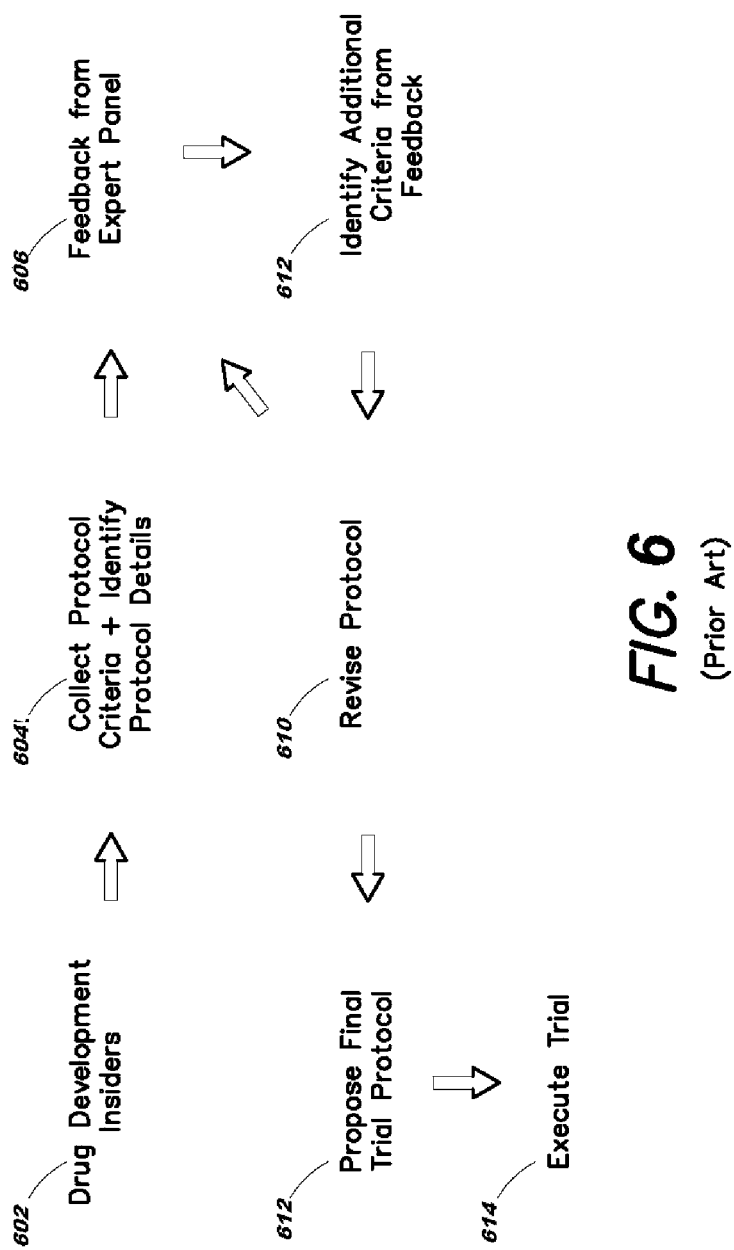
FIG. 6 illustrates an example approach to drug protocol development.

Various aspects of the system can be better appreciated with respect to an understanding of some conventional approaches to protocol development shown in FIG. 6. Illustrated in FIG. 6 is an example of conventional approaches to drug protocol development. In some conventional approaches, drug developer insiders can identify a therapeutic need and a potential drug to resolve that need at 602. The drug developer insiders collect any historic drug protocol trials that may be applicable and rely on their own experience and knowledge to identify the protocol details that will be required for human trials at 604. At 606, the protocol is reviewed by an expert panel to identify additional criteria that may be appropriate at 608 or to identify issues with the existing criteria for the protocol. The protocol can be revised at 610 and optionally reviewed and revised at 606-610. Once review and revision is complete, the final trial protocol can be proposed at 612. Various administrative bodies oversee approval of drug protocols. Requirements for approval can be stringent, especially when a proposed trial involves human subjects. If approved, the trial protocol can enter testing at 614. In some setting, issues associated with the protocol are revealed during test execution, increasing time and cost, without providing a degree of certainty that potential issues have been identified.

It is realized that drug developers and expert reviewers involved in the traditional closed approach to protocol design represent only a small portion of the population of knowledgeable persons available worldwide. When writing a clinical study protocol these scientists initially strive to clarify the rationale behind the science related to the drug development project. These scientists attempt to describe the structure and operational aspects of the project. Unfortunately, no one individual has complete knowledge of previously used clinical study protocols, thus approaches that rely on the input of small groups are often incomplete and therefore flawed.

It is also realized that considerable time and money can be saved by improving the design and review of conventional clinical study protocols. Decisions based upon research methods, clinical study populations, statistical analysis, clinical study design, clinical study procedures, and potential adverse events all can contribute to the overall cost and time it takes to complete a clinical research project. Cost factors influence a project's speed (including cycle time, planning time, timely patient enrollment), quality (including capturing data at its source, reduced error rates, automatic audit trials), and collaboration (creating a positive experience for patients, clinical investigators, study coordinators, and a sponsor's staff). By inviting the participation of a larger community of researchers, physicians, experts, patients, etc., the drug development process can be significantly improved.

Figure 7:
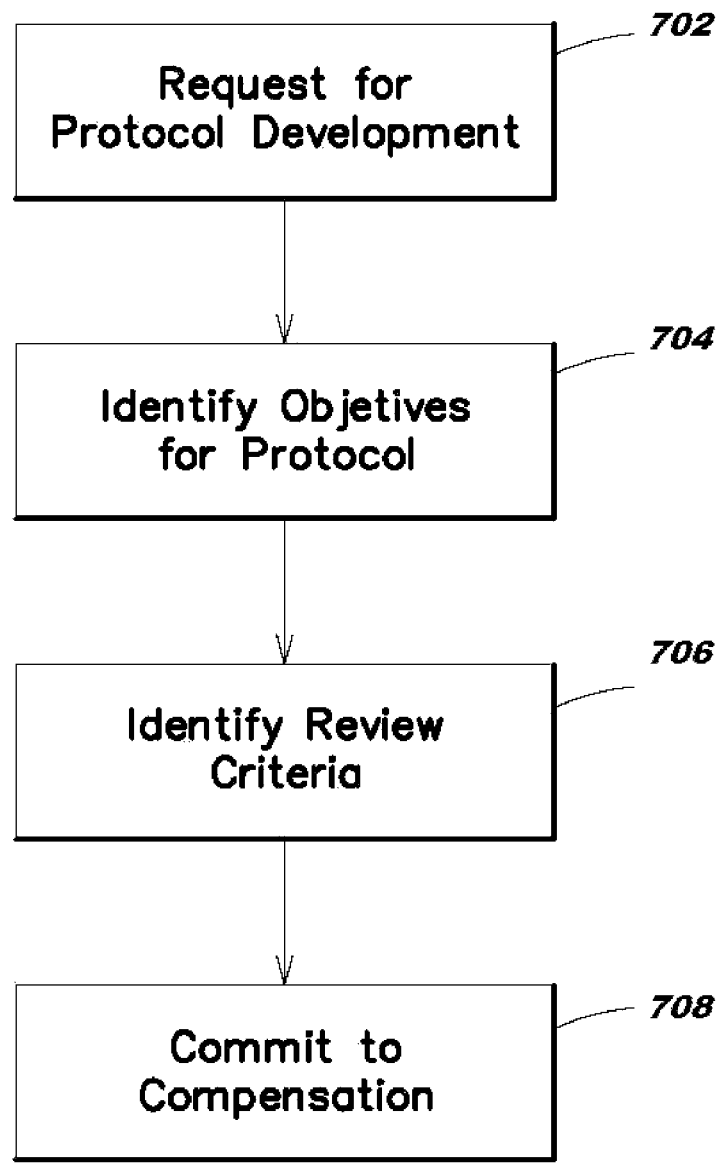
FIG. 7 is an example process for requesting development of a clinical study protocol, according to one embodiment.

Shown in FIG. 7 is an example of process flow for facilitating development of a clinical study protocol. At 702, a user prepares a request for protocol development including an overview of the protocol that will be displayed on the protocol builder system and submits the request within a user interface of the system. The requesting user can be prompted by the system to include any known objective(s) for the protocol at 704. The requestor and/or the system can identify the review criteria that will be used to evaluate responsive submissions at 706. In some embodiments, the requesting users provides their own detailed criteria. In some embodiments, the system is configured to suggest evaluation criteria that the requesting users can approve or deny. The system can also be configured to match a protocol development request to existing requests on the system, and suggest review criteria based on the matches. As part of the request for protocol development, the requesting user can commit at 708 to providing compensation to users answering the request for protocol development. The system can be configured to suggest ranges of compensation based on other protocol requests. Once the request for protocol development is complete the request can be published by the system for review by other users.

Figure 8:
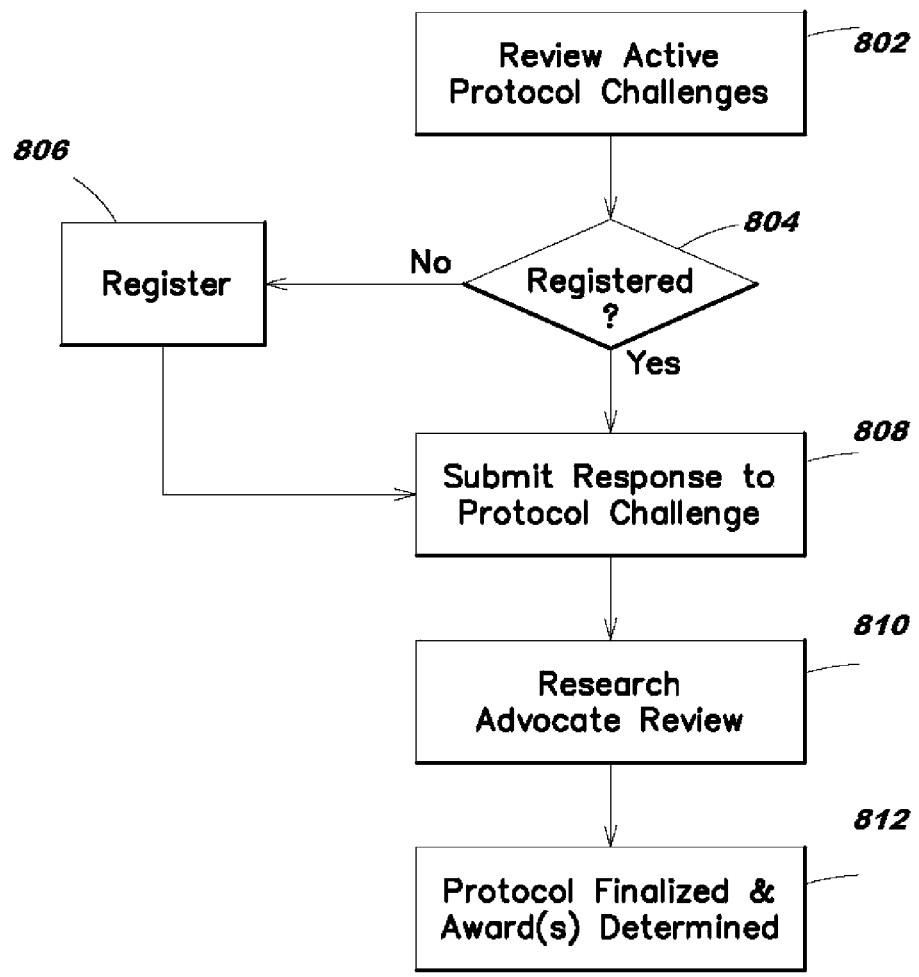
FIG. 8 is an example process flow for receiving and evaluating user submissions, according to one embodiment.

FIG. 8 illustrates an example process flow for receiving and evaluating user submissions, which can be executed by the protocol builder system. At 802, a user can review protocol challenges in a user interface of the system. Typically, the user can access the interface over the internet via a connected host computer system. Not shown, the user can access inactive protocol challenges as well as active challenges. However, in some embodiments the system is configured to only permit submission for active challenges.

Once the user has found a protocol challenge on which the user wishes to participate, the user can indicate in the user interface that he wishes to submit a response. At 804 the system determines if the user is registered. The system can request authentication information or the system can determine that the user is already registered and authenticated at 804 YES and proceed to 808. If the user is not registered 804 NO, the system is configured to request that the user register prior to submitting a response to any challenge. Registration can include additional processes executed by the system. In some embodiments, the system requests identifying information in the user interface, and further requires the user to agree to the terms of the protocol challenge and can also require the user agree to the any terms of use.

Registered users can submit their respective response to the protocol challenge at 808. The response can involve a response to part of or the entire challenge, including best approaches for research, analysis, experimental procedure, study population, inclusion and/or exclusion criteria, for example. In some embodiments, responding users are asked questions through the user interface on the protocol challenges. In some embodiments, the questions include both multiple choice and open-response formats.

In some embodiments, user submissions can be published with the protocol challenge as they are received, and users can submit comments or responses directed to other users' submissions. In other embodiments, only the protocol challenge information is published by the system, keeping responses private. In some embodiments, At 810, a research or patient advocate reviews user submissions. Review can occur during the active period of the protocol challenge. In some embodiments, the questions asked of participating users can evolve based on prior user responses. The research advocated can manage changes to the questions delivered to the participating users during the course of protocol challenge based on the review of prior submissions.

In some embodiments, the review at 810 can be repeated for each user submission, and in some embodiments at 810 can occur after the expiration of any deadline associated with the protocol development request. Review can include scoring of each response against the review criteria provided with the protocol development request. The research or patient advocate can finalize a proposed protocol in response to the review at 812. Further, the research or patient advocate can be responsible for determining awards to the participating users based on the review criteria and/or scoring assigned to each submission. In some embodiments, the research or patient advocate submits scores for each one of a set of review criteria and the system is configured to determine an award based on the scoring.

In further embodiments, review processing can also include evaluation of user comments on other user submissions. In some examples, quality metrics can be assigned to a user submission based on feedback provided by other users. In one example, a user can be presented with an option to approve another user's submission (including e.g., a challenge response). Based on a number of approvals for a given submission, a quality value can be assigned. Quality values can also modified based on disapproval received from peers.

Figure 9:
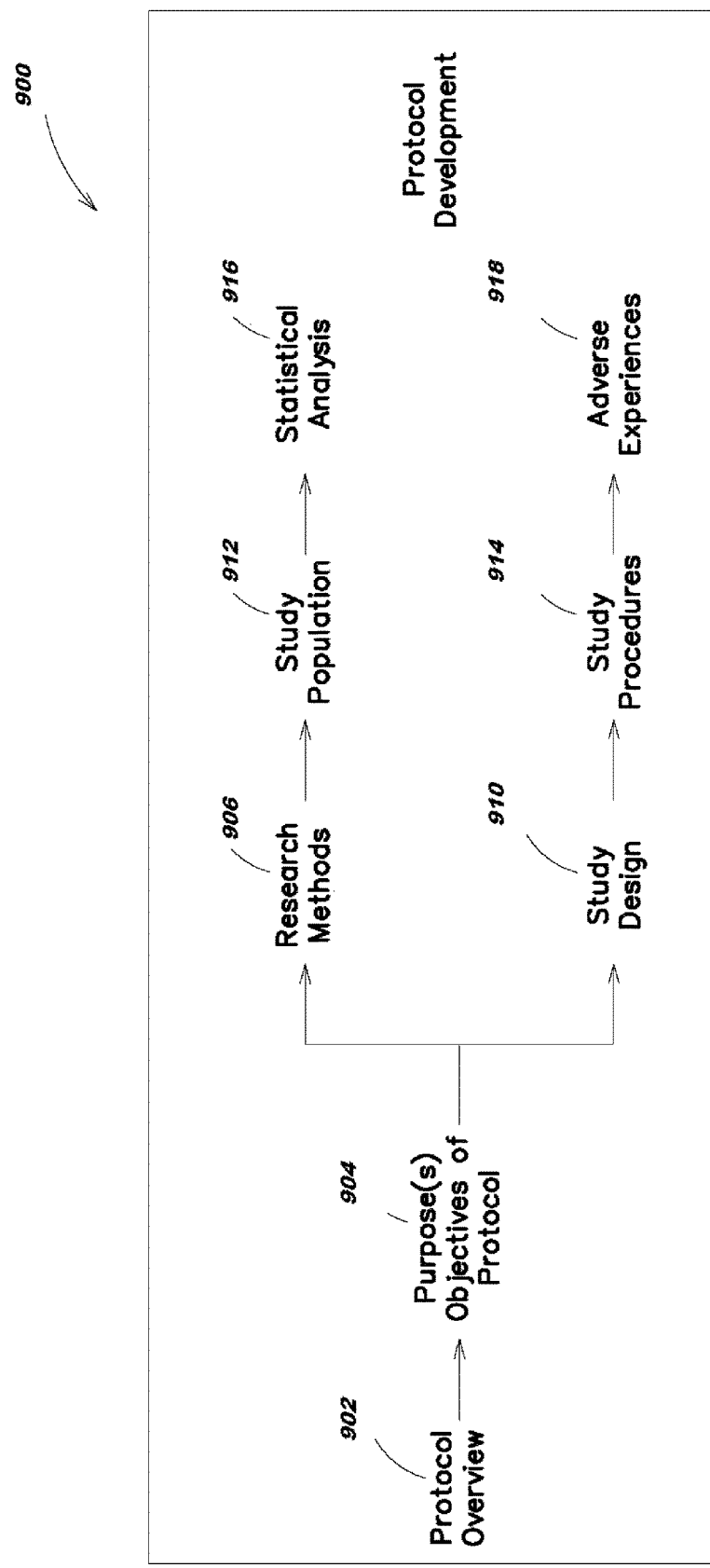
FIG. 9 illustrates an example block diagram of milestones for the development of a clinical study protocol, according to one embodiment.

The processes illustrated in FIGS. 7 and 8 can be executed together by the protocol builder system as part of an overall flow for developing a clinical study protocol. FIG. 9 illustrates an example block diagram of milestones for the development of a clinical study protocol. According to one embodiment, the protocol builder system is configured to generate a protocol overview from user submissions to the respective questions at 902. The protocol overview is used to further define purpose(s)/objective(s) of the protocol at 904. Protocol development 900 and definition can proceed along two branches as submissions responding to protocol development request are received from other users of the system. The questions and thus the responsive submissions can be targeted to elicit responses on research methods and/or study design. The protocol builder system can be configured to identify qualifying information for a participating user based on registration information, including areas of expertise, drug development history, research activity, areas of specialization, medical practice areas, etc.

Review of the respective submission can determine group opinion on research methods 906 for the protocol and any group opinion on the study design 908 parameters. Further questions can be presented by the system to arrive at the group opinion on study population at 910. Each response to the study population questions can be evaluated and/or scored to arrive at the group opinion. Development of study procedures 912, statistical analysis 914, and adverse experiences 916 can all be examined by as large of a user population as possible. Insuring the largest participating population, while providing for independent review by a research or patient advocate yields a protocol with a high level of confidence that the best process and potential issues have been identified. Additionally, providing responses to the participating community in an open format further fosters the development process by increasing the knowledge base and accelerating identification of issues within the environment. In some embodiments, the research or patient advocate can take an active role revising challenge questions as responses from the participating community are received. Received comments can also prompt the research or patient advocate to review and/or revise challenge questions in response to group opinion.

Each of the milestones illustrated in FIG. 9 can include multiple components depending on the protocol being developed and any criteria generated by a user requesting protocol development. In some embodiments, a clinical protocol overview can be generated from ideas from colleagues, experts, and world-class thought leaders. In some examples, questions on a protocol challenge are designed to elicit ideas from related published articles, and can also be designed to obtain examples from analogous projects. Development of the purposes and/or objects for any given protocol are discovered from the user population, and can also be identified from review of analogous projects, historic studies, and in some examples, can be intellectual property (confidential or otherwise) of the requesting user.

In establishing research methods, the protocol builder system is configured to generate a process for carrying out any scientific experiment associated with the clinical study protocol. In some embodiments, a duration, and criteria for measuring results will be established or improved through user submission of responses. In some examples, responses to user questions can be used to establish both dependent variables and independent variables for a protocol. A scientific experiment for validating a new drug or protocol can include, for example, a hypothesis statement or declaration of the expected outcome of the research study. The statement can be based on logical rationale and is generated so that the statement results in empirical possibilities for testing. The system can be configured to generate such a hypothesis, and can be further configured to identify testable targets during and at the completion of the experiment.

In some embodiments, the hypothesis statement can include any one or more of: (1) dependent and independent variables; (2) some type of relationship between independent and dependent variable; (3) a change in the independent variable and any effect on the dependent variable, and (4) the subjects, i.e. population being studied. For a given experiment, the independent and dependent variable define a relationship, in which one variable depends on the other variable. In the clinical study setting, a typical example can include high blood pressure and cardiovascular risk. Other independent variables and dependent variables can be identified for a study population, a treatment, a new drug, etc.

According to some embodiments, the protocol builder system is configured to provide for study population review and evaluation. The system can be configured to review and evaluate any patient recruitment plan for the clinical study which directly effects the study population that will be available for testing. In some settings the patient recruitment plan can be determined based on user responses. In some examples, implementation details for the protocol can also be reviewed, evaluated, and/or generated for inclusion in the protocol. In some embodiments, the system can review, evaluate, and/or generate: subject retention processes; estimates on the number of sites; estimates on the number of subjects required for the clinical study; among other study population parameters. The system is configured to identify and flag any procedural or safety issues that can limit feasibility. In human phase trial identification of safety risk can be tantamount to earning approval to conduct testing.

The protocol builder system can be further configured to establish guidelines for statistical analysis. In some examples, primary statistical analysis can be modeled on previous studies. The overall statistical methods can be selected by the system, and/or confirmed by the user population. The statistical methods can be then employed along with the determination of both the dependent and independent analysis variables identified as part of the research methods. Examples of establishing dependent and independent variables can include establishing measureable baseline and treatment characteristics to be used in the study. Other variables can be defined by the system to cover both sample size and target study population for any statistical analysis.

The system can also include a template library of previous research methods, potential research methods, and ongoing research methods that can be matched by the system to a request for protocol development. The previous research methods, potential research methods, and ongoing research methods can be referenced in the questions presented to the user population. The response to those questions can be evaluated to determine a best approach with a high degree of confidence. In some embodiments, previous research methods, potential research methods, ongoing research methods, and/or publically available research methodologies can be stored as part of a template library. The template library can be accessed by the system to select element of any template, which can be combined into a complete research method. The system can be configured to present questions to the user population to identify templates and/or template elements for incorporation into a research methodology. In some embodiments, the system can be configured to automatically obtain information form electronic sources for inclusion in the template library. In addition, automatically obtained information can be subject to review prior to inclusion in the template library. In some examples, the system is configured to require review of a research or patient advocate prior to inclusion in the template library.

Example templates and template elements can include: drug/medical device/interventions schedule, modifications, precautions; device implantation procedures; dose modifications (which can also include one or any combination of: drug preparation information, drug administration information, drug storage information; drug/device accountability, retention, final disposition; required concomitant medications, if applicable; and treatment duration); information and/or evaluation of scientific need balanced against with subject burden; timeframe considerations including any consideration of time to collect data and accommodate enrollment; timeframe considerations including any limiting period to time necessary to insure collection of data to evaluate study endpoint; and definition of clinical endpoints (which can include one or any combination of: identifiable changes that shows the proposed intervention did what it was supposed to do; primary endpoint which measures the specific clinical effect the intervention is preventing/treating (e.g., patient survival, resolution of disease, etc.); and surrogate endpoints which measure changes in symptom/biological indicator for the success of the intervention (e.g., T-cell count, radiographic imaging, etc.)). Each template and/or template element can be categorized to reflect a type of study, a field of medicine, intended result, which the system can employ to match template and/or template elements to protocol development requests.

According to some embodiments, the system can be configured to evaluate any proposed protocol for ethics/human subject protection concerns as part of the determination of the study procedures. The system can be configured to evaluate any one or combination of: clinical study participant burden, appropriateness of including participants less than 18 years of age (if applicable) related to the expected risks and prospect of benefit. The questions delivered to user participants are configured to establish broad community agreement that identifies any ethical issues related to the proposed protocol.

The protocol builder system can be further configured to determine adverse experiences for any protocol challenge and/or request for protocol development. Examples of adverse experiences can include any one or combination of: safety; identified safety concerns; special safety concerns that an experimental intervention may raise; and identification of established safety profiles for medication(s) being tested.

According to some embodiments, the system can be further configured to generate clinical endpoints as part of the protocol development and/or evaluation. In some examples, clinical endpoints with clearly defined and measureable stopping points are defined. In some examples the endpoints can be defined based on interim and/or ongoing analysis of test results during test execution. Other endpoints can be defined by the user requesting protocol development. In some examples, a research or patient advocate can generate clinical endpoints and include them as requirements for the protocol. Further, the system can be configured to accept input from a review committee in generating, determining, and/or approving clinical endpoints. In some embodiments, the review committee can define clinical endpoints that must be followed for a given protocol. In addition, physician review can also be employed and any endpoint adhered to as part of the protocol. Example clinical endpoints can also establish criteria for terminating a trial if a clear benefit is shown, if a certain pre-determined proportion of adverse events occur, and/or if endpoints are not being met.

Figure 10:
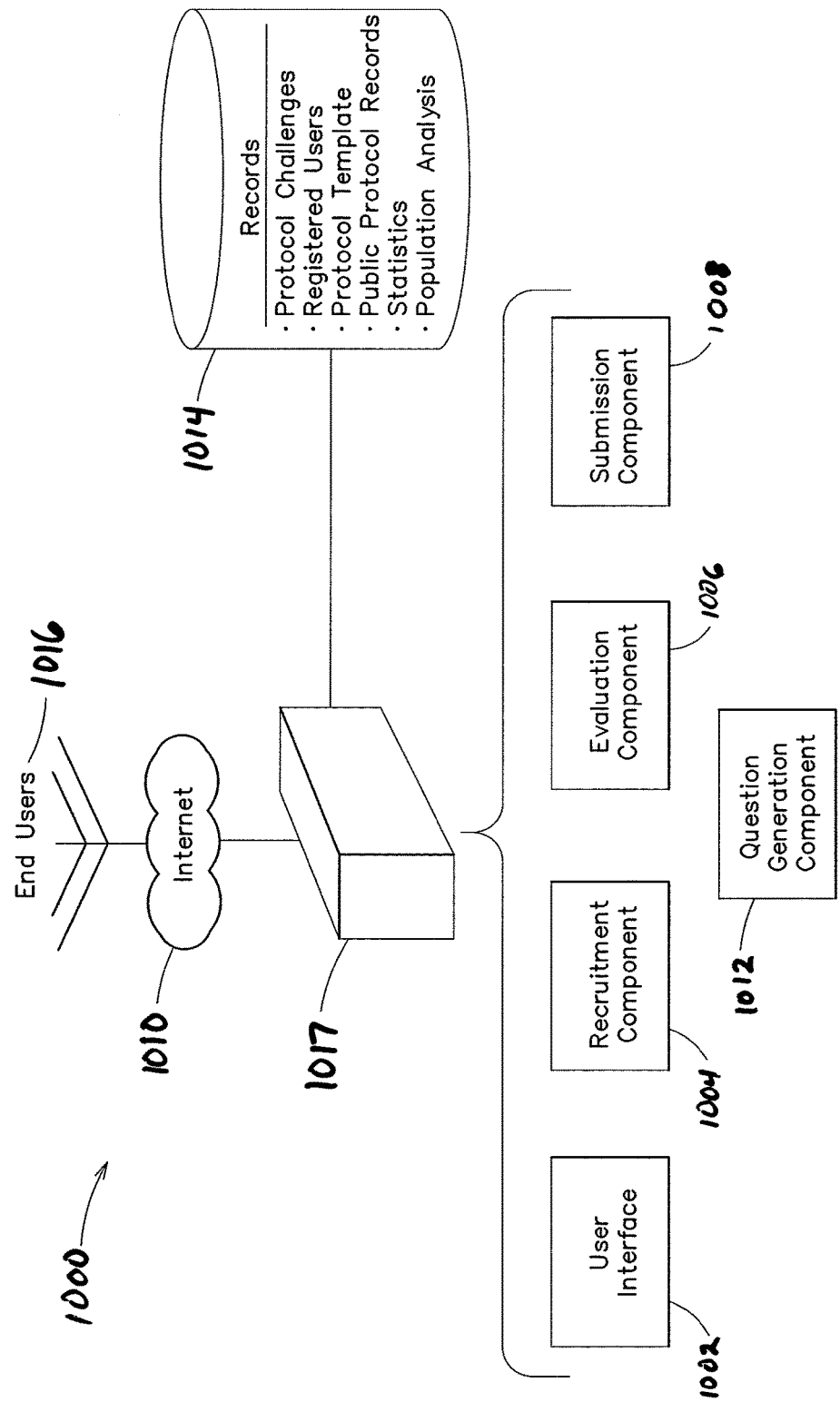
FIG. 10 is an example a block diagram of an example protocol builder system, according to one embodiment.

Various components of the protocol builder system can be configured to develop part or entire protocols. Shown in FIG. 10 is a block diagram of an example protocol builder system. The system can include a user interface accessible over a communication network (e.g., Internet 1010). The system can also include a recruitment component 1004 configured to identify and deliver invitations to potential users. Potential users can be matched to protocol challenges submitted to the system and target invitations delivered to the potential users to increase user feedback on given protocols. In some examples, a matching component can be configured to identify an expert in a particular field, a particular therapeutic area, medical practice area, among other options. Invitation can be targeted to the identified experts by the recruitment component based on information obtained from the matching component. In some embodiments, the matching component can be configured to poll the Internet to obtain matches to current protocol development projects. In other embodiments, the matching component can review information stored in a template library or other database to identify matching users.

Further matching can also be made against registered users and/or any information stored on registered users in the system database 1014. The system can be configured to deliver notifications to registered users based on matches between information on the protocol development project. The notifications can include notices that protocol development projects are underway in that are in their field of interest, area of expertise, practice area, etc. In some embodiments, users can identify areas of interest and/or areas of expertise in which they wish to receive notifications. In some examples, user preferences can be stored as part of a user profile.

In some embodiments, user submissions can be evaluated by an evaluation component 1006 which can be configured to assign scores and/or identify agreement on protocol development. The evaluation component can be further configured to present user submissions to a research or patient advocate who assigns scores to the user submissions. The user interface 1002 can be configured to interact with a submission component 1008, which permits submission of protocol development requests and submission of user ideas on protocol development. In one embodiment, the submission component can be configured to verify that user responses/submissions meet the requirements of a given protocol development request. The submission component can be further configured to prompt users for required information in a protocol development request. For example, the submission component can require information on a category to assign to the request, intended result of the protocol, a drug to evaluate, etc. The submission component can be configured to require definition of review criteria in a protocol development request, among other options.

In some embodiments, the submission component 1008 can also be configured to accept user submissions regarding other user contributions submitted to the system. In particular, the submission component 1008 can be configured to enable users to agree and/or disagree with contributions posted on the system by other users. Peer review of user contributions can then inform evaluations of the reviewed material, both by advocates and by automated processing performed by system.

System 1000 can also include a challenge generation component 1012, configured to access a template library stored on system 1000. The storage for system 1000 can include for example a database 1014. Database 1014 can be located on server 1017 and store information on protocol challenges, protocol development requests, registered user information, invitation criteria, template libraries, protocol templates, public protocol records, statistics, population analysis, statistical models among other examples. The challenge generation component is configured to identify questions presented to end users 1016 accessing the protocol builder system through, for example, respective host computer systems. The challenge generation component is configured to analyze submitted protocol development requests and identify existing protocol template and/or template elements that are applicable to the development request. The challenge generation component can be configured to present matching questions, templates, and/or template elements to a research or patient advocate for inclusion in the protocol development request. The challenge generation component can be configured to modify and/or update questions presented to users based on received responses. Further the challenge generation component can be configured to select from a population of questions for the protocol challenge based on information associated with a responding user. In some embodiments, the component can match information on profession, specialty, work experience, etc. to identify questions that the participating user is especially qualified to answer.

The various components of system 1000 can be configured to operate together to perform processes for generating a drug trial protocol, for example, by executing the processes illustrated in FIGS. 7-8. The components of system 1000 can be executed by a processor from memory to allow the system to provide for the operations and/or functions discussed above. In some embodiments, system 1000 can include additional components. In one example, system 1000 includes a natural language processor configured to parse user submissions. Based on the parsed submissions, the natural language processor (NLP) can assist in automated evaluation of user submissions. In some examples, the NLP can be configured to parse submissions and communicate the results to an evaluation component. The NLP can also be configured to capture information from publicly available sources including protocol publications made available by the FDA. Captured information from public sources can be matched against user submissions and/or drug protocol development projects, for example. The matched information can be incorporated by the system in developing questions for users. In some examples, matched information can be provided to a research or patient advocate for review prior to inclusion in any project.

The NLP can also be configured to process Internet based resources for matching drug protocol development projects against potential users. In one example, various publications can describe a given user's expertise in a field. A match between an ongoing drug protocol development project and user experience, for example, can be identified. The matched records can be made available to a recruitment component, for example 1004, and an invitation delivered to any contact information extracted for the user.

Matching can be employed to identify matches on registered users, potential users, and drug protocol development project characteristics. In some setting, existing drug protocols and their clinical study protocol are available. Matching characteristics between existing clinical study protocols can yield information on study population, study design, etc. Any matching information can be incorporated into a drug protocol development process. Additionally, a research or patient advocate can curate the introduction of matching information into the protocol development process.

In some embodiments, a clinical study protocol can be collaboratively developed. Evaluation of the developed protocol can include a determination that the clinical study protocol meets or does not meet defined protocol endpoints during execution of the clinical study protocol. In some embodiments, an evaluation component is configured to track and evaluate the execution of a clinical study protocol. In particular, some embodiments of the system can accept input of data from an executing clinical study protocol. The input data can be evaluated by the evaluation component, e.g., 1006. In some embodiments, a research or patient advocate is assigned to evaluate the input data and any results extrapolated from the data. The research or patient advocate can determine if defined endpoints have been met, will be met, or in some examples cannot be met. The determination on the endpoint can impact awards for participants. In some embodiments, awards can be contingent on meeting defined endpoints of a clinical study protocol, in others meeting the defined endpoints can be considered as a factor. Each drug protocol development can set different evaluation criteria.

Figure 11:
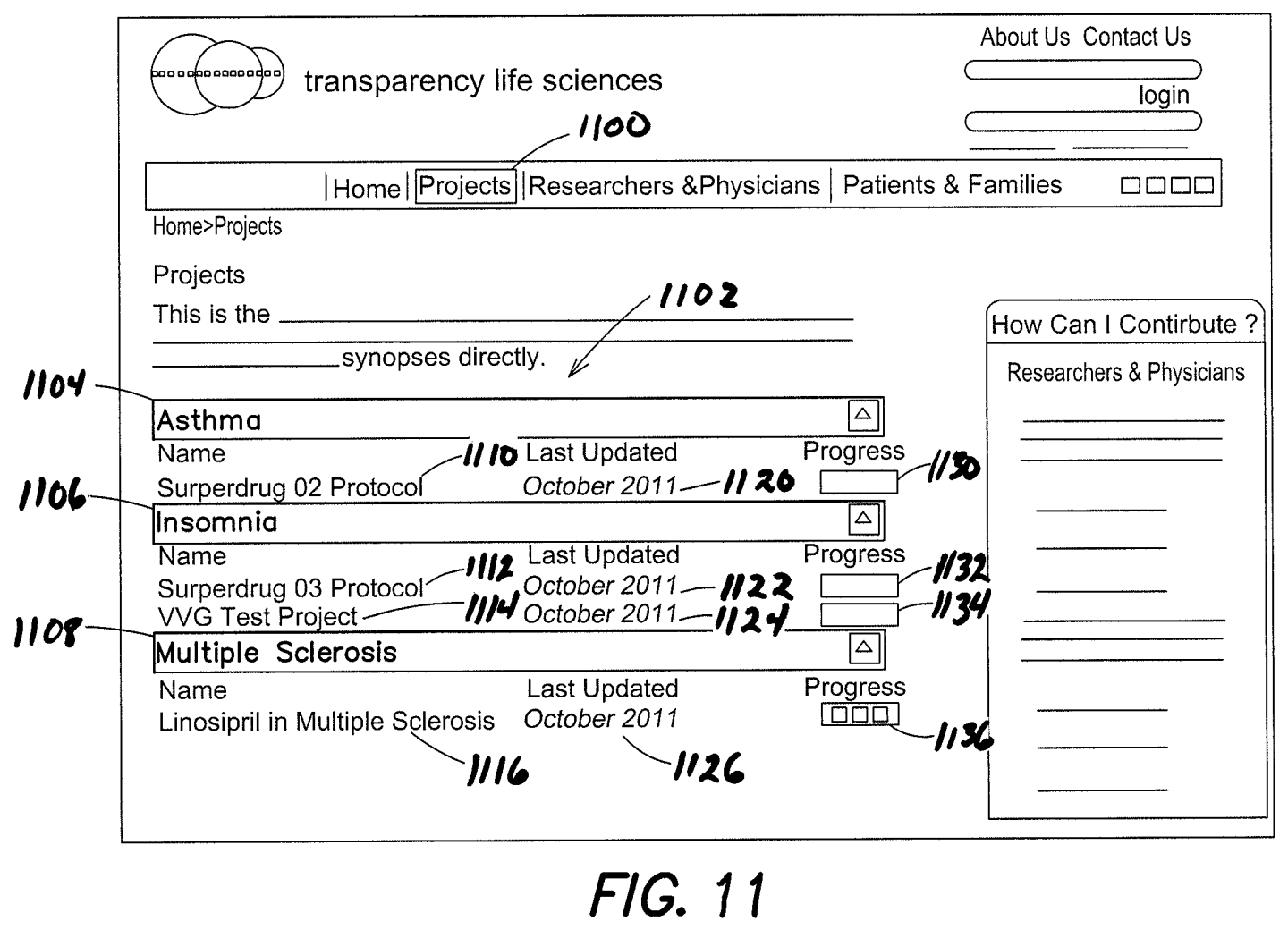

Shown in FIG. 11, is a screen capture of an example user interface. The user interface provides public access to a "Projects" page at 1100. The projects page provides access to current protocol development projects. In some embodiments, inactive projects can also be shown. At 1102 a frame of the user interface is displayed, which is configured to display active protocol development projects. The user interface is further configured to display the active projects based on category and/or field associated with the protocol development projects. Shown at 1104-1108 are examples of categories assigned to protocol projects. Examples categories include Asthma 1104, Insomnia 1106, and Multiple Sclerosis 1108. Other categories can be supplied by a protocol builder system. The categories can be based on fields of medical specialization, for example, cardiology, urology, neurology, infectious diseases, among other. Categories can also include definition of a therapeutic area. Each project 1110-1116 is assigned a name that is displayed in the user interface. Additional information can be displayed with each project, including a last access date 1120-1126, and a progress indicator 1130-1136. Progress for a project can be determined automatically by the system, and in some embodiments, progress can be determined based on review by a research or patient advocate.

In some examples, access to individual projects 1110-1116 is restricted to registered users. In response to selection of any of the individual projects 1110-1116, the user interface is configured to bring the user to a registration screen. An example registration screen is shown in FIG. 12. The user interface is configured to require information for a registering user. For example, the user is asked to establish a user name at 1202. Contact information is required at 1204. The user wishing to register also specifies and confirms a password to associate with their account at 1206-1208. Background information can be requested in the user interface. In some examples, a therapeutic area may be required to proceed with registration. At 1210, the user wishing to register can identify a therapeutic area that the user is, for example, experienced in or wishes to participate in.

Personal information can be required. In some embodiments, First Name 1212 Last Name 1214 can be required for registration. Additional information can be optionally input into the user interface, for example: middle initial 1216, suffix 1218, salutation 1220, phone number 1222, degrees(s) earned 1224, and job title 1226. The user interface can also be configured to upload an image 1228 to associate with the user account. In some examples, the user wishing to register can identify a role that the user has performed in drug development at 1230. Once the required information is input and any optional information is supplied, registration can continue by selecting submit at 1232 in the user interface. In some embodiments, the user wishing to register is asked to review and agree to a "Terms of Use" for the site. In some embodiments, the user must agree to the terms in order to complete registration and participate in the protocol development process.

Figure 13:
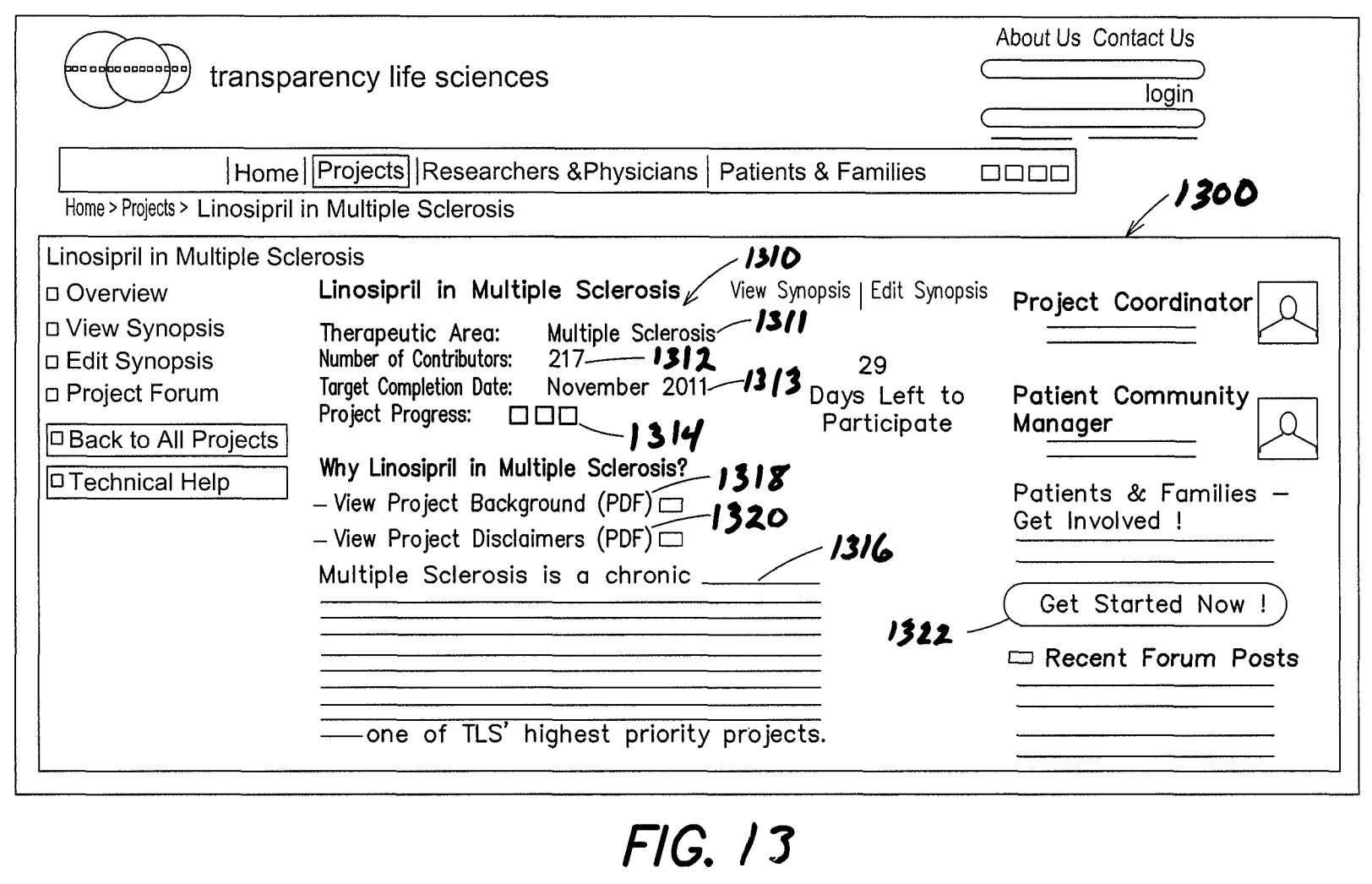

Registered users are permitted to access details associated with a given protocol development project. Various projects can have different targets, including for example, establishing a protocol to test a new drug, establish a protocol to improve drug testing, develop a protocol for a new therapeutic approach, and develop a protocol to improve a therapeutic approach. Shown in FIG. 13 is a screen capture of an example protocol development project detail screen 1300. The project detail screen 1300 includes information on the project and current state at 1310. Project information can include Therapeutic Area at 1311; Number of Contributors at 1312; Target Completion Date at 1313; and Project Progress at 1314. A synopsis of the protocol development project is display at 1316. Links to any documents associated with the project can be displayed in screen 1300, for example, at 1318 and 1320. In some examples, links to additional terms and/or review criteria for the protocol development project can be provided as links to documents shown in screen 1300.

According to some embodiments, the user interface is configured to display screen 1300 to registered users accessing a protocol builder system over the Internet. The user interface can further be configured to permit registered users to participate in the protocol development project by selecting a hyperlink in the user interface. For example, "Get Started Now" at 1322 in the user interface can be configured to allow users to being participating in challenges associated with the protocol project. In some embodiments, selection in the user interface of Get Started Now at 1322 causes the user interface to transition to a set of challenges associated with the protocol development project. For a given protocol development project, multiple types of challenges can be available. In other examples, challenge questions can be displayed in the project detail screen directly.

For example, shown in FIG. 14 is a screen capture of an example challenge screen 1400 including challenge questions, which can be displayed as its own page, or can be displayed as part of a project detail screen. In some examples, screen 1400 can be displayed as a portion of a protocol project detail screen 1300. In some embodiments, screen 1400 can be configured to display separately accessed by for example a hyperlink in a protocol project detail screen.

Challenge screen 1400 includes tabs at 1402 and 1404 for separating the display of the two types of challenges available in the displayed protocol development project. Additional types and display tabs can be available in addition to tabs 1402 and 1404. Tab 1402 is currently visualized in the display of screen 1400. Selection of tab 1404 causes the system to display the challenges of type "Patient Challenges." Multiple pages of challenges (e.g., FIG. 15, page 1500) for each type can exist and be displayed in a user interface of a protocol builder system. The challenges presented can be organized based on topic, for example, clinical study population at 1406. The challenges can also be organized based on steps of overall protocol development (as shown e.g., in FIG. 9 at 902-916). The user can be asked to answer questions associated with a topic before proceeding to additional question on another topic of protocol development. For patient population, the challenge questions can be configured to elicit the best patient population for a given phase of a protocol development plan.

In some embodiments, possible answers to challenge questions can be presented to the user for selection on a YES/NO basis at 1408. Further, multiple selections can be input in the user interface in response to challenge questions, including for example, multiple choice selections (not shown). In some examples, a third option can include "never" to indicate that a particular patient population would not be appropriate for a particular drug protocol development project. Such answers can be tracked, and optionally reviewed for soundness. The tracked answers can be used for future drug protocol development projects to include and/or exclude candidate patient populations from challenge questions.

At 1408, the user interface displays a series of candidate patient populations. Candidate populations can be identified during creation of a drug protocol development project. In some examples, a user can submit a request for a drug protocol development project which includes user identified patient populations. In addition, a submission component can be configured to match information submitted in the request for a drug protocol development project or other information available on a protocol builder system to existing protocols having identified patient populations. Based on matches between the information submitted and existing protocols, the system can automatically present the identified patient populations as candidate patient populations. The system can be configured to automatically identify some or all of the patient populations. In some embodiments, the system can be configured to augment user supplied patient populations.

In some embodiments, the protocol builder system can be configured to present the identified and/or submitted patient populations to a research or patient advocate for review. The system can be configured to require approval of a research or patient advocate prior to presenting candidate populations as challenge questions. In some embodiments, a submission component can be accessed by a user external to the system for inputting a drug protocol development project. In addition, the submission component can also be accessed by administrative users (e.g., system administrators, research advocates, patient advocates, review committees, etc.) who can also input drug protocol development requests. In some settings, protocol development requests are submitted to administrative users, reviewed, and then made available to the registered users of the protocol builder system.

Once candidate patient populations are identified and optionally approved, the candidate patient populations are presented within challenge questions, for example, shown on page 1400 at 1408. Example patient populations include clinically isolated syndrome 1410; relapsing remitting 1411; primary progressive 1412; secondary progressive 1413; and progressive—relapsing 1414. In some embodiments, additional patient populations are presented. Further, already executed drug trials can include additional patient population definitions that have been explored in a clinical trial setting, each of these populations is made available for matching by the system, and any of the additional patient populations can be included. In some examples, additional patient populations can be evaluated by presenting each as a challenge questions. In addition to executed trials as a source of patient populations, literature on patient population definition can also be presented, and challenge questions formulated to target patient populations definitions presented in available literature.

In some embodiments, the system can be configured to poll existing literature for protocol development ideas and concepts, including any ideas and concepts specific to drug protocol development. Any matching literature can be stored on the system, and used in subsequent review by, for example, the submission component, to identify candidate patient populations. Protocol development literature can be readily identified using the Internet and known search algorithms, and/or known search engines. The protocol builder system can be configured to automatically retrieve and store protocol development literature and/or information on executed trials from publically accessible sources. In some embodiments, the system can be configured to automatically execute searches for protocol development literature and/or information on executed trials. In some embodiments, a matching component can identify search criteria based on information associated with input protocol development requests and/or current protocol development projects.

The protocol builder system can be further configured to identify categories of interest for any trial or literature, based on, for example, therapeutic area, medical practice area, defined patient populations, clinical goals, and/or application drug protocol milestones (e.g., as illustrated in FIG. 9). In some embodiments, each identified category of interest can be stored and used for matching against protocol development projects. In one example, the stored literature and/or executed trial literature can be parsed to identify information of interest and the parsed information used in matching against protocol development projects.

In addition to trial information and literature obtained by the system, the registered users can also suggest additional patient populations and/or provide their reasoning for selecting/rejecting specific patient populations in 1416. The answers provided to the challenge question, as well as the reasoning provided can be evaluated in determining a score for a user's contribution to the development project. Each challenge can be scored separately. In some embodiments, points can be awarded based on scoring of the user's contribution. In some examples, points can be accumulated to redeem awards. In other examples, points can be exchanged for good and/or services. In some embodiments, points can be awarded based on review by a research or patient advocate, automated review by an evaluation component, and in others by a combination of research or patient advocate and automated review. The review criteria that the system employs can be presented in a protocol project detail screen, e.g., 1300 via link 1320. In some embodiments, the system can be configured to require agreement to any additional terms associated with a specific project prior to allowing a user to submit responses to challenge questions.

Multiple challenges can be organized into multiple topics (e.g., 1406 and 1420) each having challenge questions. At 1420, a second challenge topic is display in the user interface regarding regulatory strategy for the protocol development project. At 1422 the user interface displays the challenge question "Could lisinopril be developed for MS using the 505(b)2 path?" At 1424 the user is prompted for a yes no response. Other development paths can be displayed. Further, the user's reasoning for the response is requested at 1426. As discussed above, a user requesting a protocol development project can input candidate paths for challenge questions, additionally the protocol builder system can be configured to automatically identify candidate paths. In some embodiments, all identified paths (e.g., by the user, by the system) are reviewed and approved before being incorporated into challenge questions. Information on executed trials can be stored on the system, and matches between previously executed trials and information for a current protocol development project used to identify candidate paths. Additionally, protocol development literature describing development paths can be matched to information in a protocol development project, and any described development path(s) automatically suggested by the system for inclusion in a protocol development project.

In addition, registered users can suggest additional candidate development paths via the user interface, e.g., at 1426. According to some embodiments, research or patient advocates review challenge answers and any reasoning submitted during the course of a protocol development project. Additional candidate paths can be identified and challenge questions modified or augmented to include new candidate development paths based on submitted comments.

At 1430, a button configured to provide access to additional challenge topics and/or questions is displayed. In response to user selection, button 1430 caused the system to display any additional pages of challenge topics and associated questions (e.g., FIG. 15 page 1500).

Additional challenge topics and questions can be accessed from screen 1400, in response to selection of 1404 in the user interface. The protocol builder system is configured to solicit and process input from drug developer experts as well as patients. Patients can contribute their knowledge of clinical procedures to the protocol development project. Patient challenges can be presented in the user interface organize by topic, for example, as displayed at 1408. Multiple challenge topics can be presented to users who wish to participate in patient challenges. In some embodiments, users can identify therapeutic areas in which they have experience or wish to participate in during registration. Additionally, user can identify that they wish to participate in patient challenge development. In some settings, user's can participate as either patient participants or research participants with different challenges being presented to the different user populations based on their registration selection. In some embodiments, users can participate in either category of challenge, and can transition between research directed challenges and patient directed challenges by selecting portions of the user interface.

Various embodiments according to the present invention may be implemented on one or more specially programmed computer systems, including for example FIG. 10 protocol builder system 1000. These computer systems may be, for example, general-purpose computers such as those based on Intel PENTIUM-type processor, Motorola PowerPC, AMD Athlon or Turion, Sun UltraSPARC, Hewlett-Packard PA-RISC processors, or any other type of processor, including multi-core processors. It should be appreciated that one or more of any type computer system may be used to facilitate hosting a curated environment for open development of clinical trial studies and in particular clinical trial studies for drug testing according to various embodiments of the invention. Further, the system may be located on a single computer or may be distributed among a plurality of computers attached by a communications network.

A general-purpose computer system according to one embodiment of the invention is specially configured to perform any of the described functions, including but not limited to, creating, storing, parsing, matching, evaluating, and displaying protocol development projects, project details, and challenge questions and/or answers associated with a protocol development project, etc., and the invention is not limited to having any particular function or set of functions.

Figure 16:
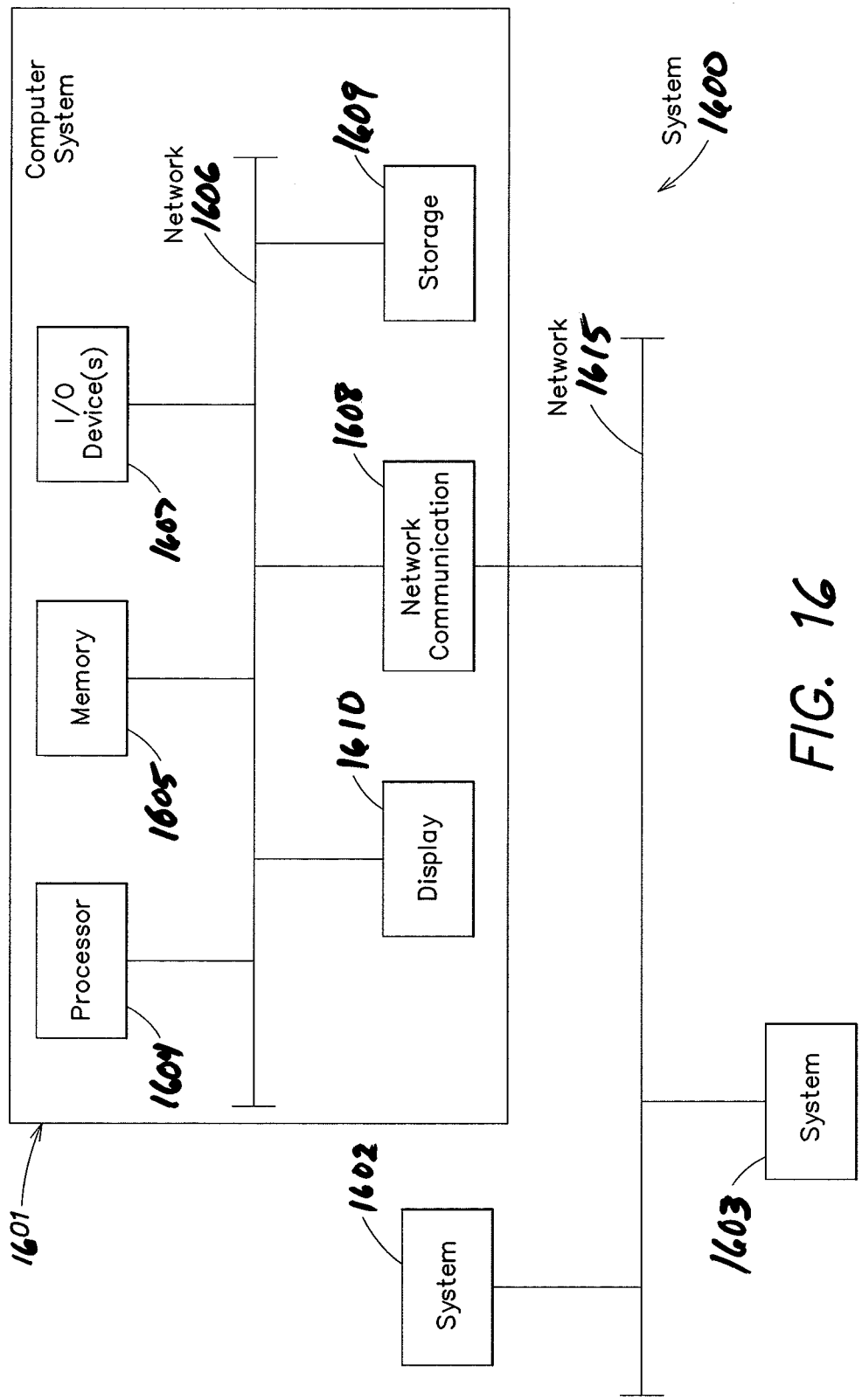
FIG. 16 is a block diagram of one example of a computer system that may be used to perform processes and functions disclosed herein.

FIG. 16 shows a block diagram of a general purpose computer and network system 1600 in which various aspects of the present invention may be practiced. For example, various aspects of the invention may be implemented as specialized software executing in one or more computer systems including general-purpose computer systems 1601-1603, shown in FIG. 16. The computer systems 1601-1603 may include a processor 1604 connected to one or more memory devices 1605, such as a disk drive, memory, or other device for storing data. Memory 1605 is typically used for storing programs and data during operation of the computer system. Components of computer system may be coupled by an interconnection mechanism such as network 1606, which may include one or more busses (e.g., between components that are integrated within a same machine) and/or a network (e.g., between components that reside on separate discrete machines). The interconnection mechanism enables communications (e.g., data, instructions) to be exchanged between system components of the system 1601.

Computer system also includes one or more input/output (I/O) devices 1607, for example, a keyboard, mouse, trackball, microphone, touch screen, a printing device, display screen, speaker, etc. Multiple displays can be included in computer system 1601, e.g., display 1610. Display 1610 can be a separate device, and integrated display, and can be configured to display in a plurality of display formats. In addition, computer system may contain one or more interfaces (e.g., network communication device 1608) that connect computer system to a communication network 1115 (in addition or as an alternative to the network 1606).

The storage system 1609, typically includes a computer readable and writeable nonvolatile recording medium in which signals are stored that define a program to be executed by the processor or information stored on or in the medium to be processed by the program. The medium may, for example, be a disk or flash memory. Typically, in operation, the processor causes data to be read from the nonvolatile recording medium into another memory that allows for faster access to the information by the processor than does the medium. This memory is typically a volatile, random access memory such as a dynamic random access memory (DRAM) or static memory (SRAM). The memory may be located in storage system, as shown, or in memory system. The processor generally manipulates the data within the memory 1605, and then copies the data to the medium associated with storage after processing is completed. A variety of mechanisms are known for managing data movement between the medium and integrated circuit memory element and the invention is not limited thereto. The invention is not limited to a particular memory system or storage system.

The computer system may include specially-programmed, special-purpose hardware, for example, an application-specific integrated circuit (ASIC). Aspects of the invention may be implemented in software, hardware or firmware, or any combination thereof. Further, such methods, acts, systems, system elements and components thereof may be implemented as part of the computer system described above or as an independent component.

Although the computer system of FIG. 16 is shown by way of example as one type of computer system upon which various aspects of the invention may be practiced, it should be appreciated that aspects of the invention are not limited to being implemented on the computer system as shown. Various aspects of the invention may be practiced on one or more computers having a different architectures or components that that shown in FIG. 16. The system 1600 can execute the process illustrated in FIG. 18, and/or components of a system (e.g., system 500) can be configured to execute the process illustrated in FIG. 18.

Figure 18:
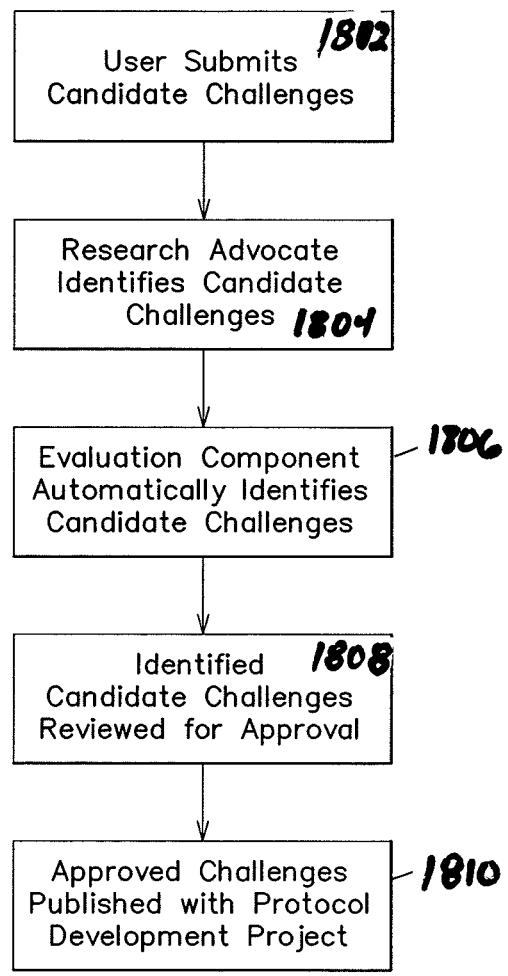
FIG. 18 illustrates an example process for approving challenges for protocol development, according to one embodiment.

In FIG. 18, the example process begins at 1802 with user submission of candidate challenges. In some embodiments, in addition to user submission, research or patient advocates can also identify candidate challenges at 1804. In other embodiments, an evaluation component can be configured to automatically identify candidate challenges at 1806. In some implementation, one or more sources can be used to identify candidate challenges (i.e., one or more of 1802, 1804, and 1806). At 1808 any identified challenges are reviewed for approval. At 1810 the approved challenges are published with a protocol development project.

Figure 19:
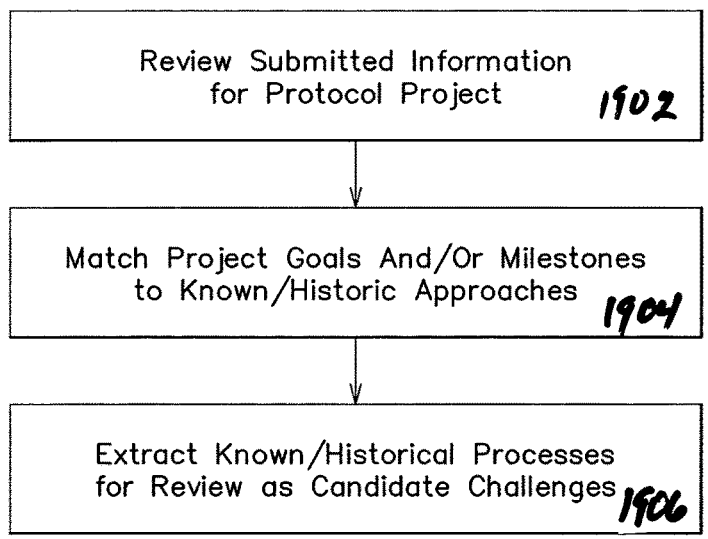
FIG. 19 illustrates an example process for matching protocol projects, according to one embodiment.
Figure 20:
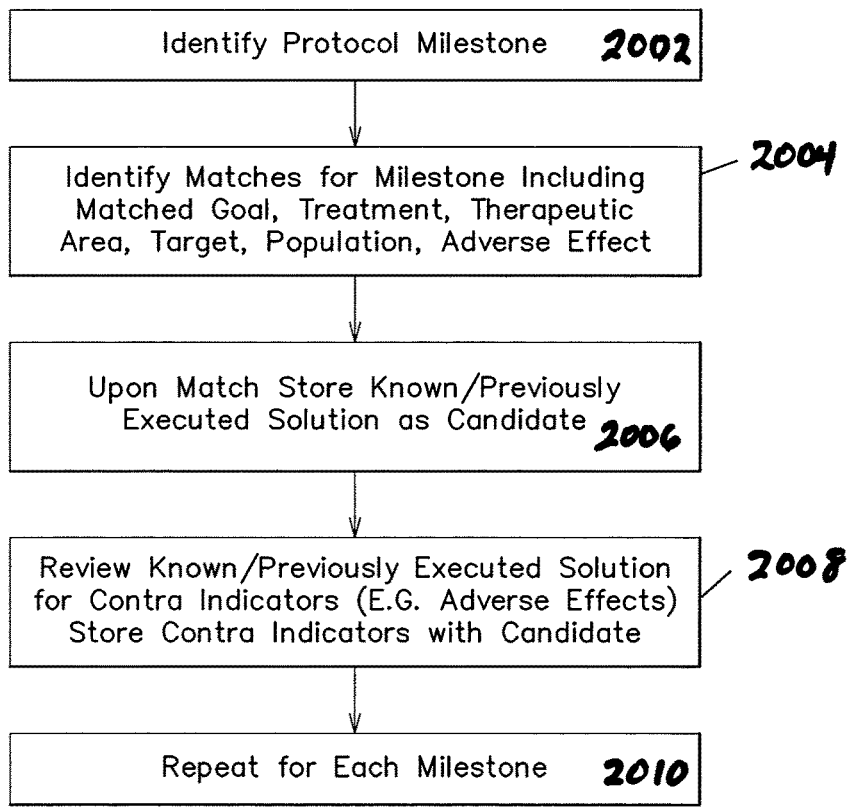
FIG. 20 illustrates an example process for matching protocol information, according to one embodiment.

The process executed on such systems can include also other processes, for example, illustrated in FIGS. 19-20. FIG. 19 illustrates an example process for matching protocol projects to known and/or existing clinical protocols. The matched approaches can then be presented as candidates for review. As shown, the process begins at 1902 with review of information submitted for a protocol project. The information can be matched (e.g., 1904) to known approaches, and information from known approached can be extracted at 1906 based on any matches. FIG. 20 illustrates a pseudo code process for matching protocol information to known/existing approaches to generate candidate challenges for review. FIG. 20 also illustrates extracting contra indicators that can reflect disadvantages to using a given candidate as a protocol challenge. The process begins at 2002 with identification of protocol milestones. Information for the milestone can be matched against known approaches at 2004. Any matched can be used to capture and store known solutions at 2006, and/or known approaches associated with specific milestones. The approaches can also be captured with any additional information (e.g., indicating success or failure, among other options). At 2008 any matches on known/previously executed approaches can be reviewed to establish any contra indicators. At 2010, the analysis can be repeated for each milestone in a given protocol. As discussed, the processes shown in FIGS. 19-20 can be executed on general purpose computer systems.

The computer system may be a general-purpose computer system that is programmable using a high-level computer programming language. The computer system may be also implemented using specially programmed, special purpose hardware. In the computer system, processor is typically a commercially available processor such as the well-known Pentium class processor available from the Intel Corporation. Many other processors are available including multi-core processors and microprocessors. Such a processor usually executes an operating system which may be, for example, the Windows-based operating systems (e.g., Windows NT, Windows 2000 (Windows ME), Windows XP, Windows VISTA, Windows 7 operating systems) available from the Microsoft Corporation, MAC OS System X operating system available from Apple Computer, one or more of the Linux-based operating system distributions (e.g., the Enterprise Linux operating system available from Red Hat Inc.), the Solaris operating system available from Sun Microsystems, or UNIX operating systems available from various sources. Many other operating systems may be used, and the invention is not limited to any particular operating system.

The processor and operating system together define a computer platform for which application programs in high-level programming languages are written. It should be understood that the invention is not limited to a particular computer system platform, processor, operating system, or network. Also, it should be apparent to those skilled in the art that the present invention is not limited to a specific programming language or computer system. Further, it should be appreciated that other appropriate programming languages and other appropriate computer systems could also be used.

One or more portions of the computer system may be distributed across one or more computer systems coupled to a communications network. These computer systems also may be general-purpose computer systems. For example, various aspects of the invention may be distributed among one or more computer systems (e.g., servers) configured to provide a service to one or more client computers, or to perform an overall task as part of a distributed system. For example, various aspects of the invention may be performed on a client-server or multi-tier system that includes components distributed among one or more server systems that perform various functions according to various embodiments of the invention including displaying, accessing, evaluating drug protocol development projects, as examples. Other components can be configured to execute recruitment functions, poll electronic resources for protocol development literature and/or executed drug trials, parse electronic resources for matching to current drug protocol development projects, etc. These components may be executable, intermediate (e.g., IL) or interpreted (e.g., Java) code which communicate over a communication network (e.g., the Internet) using a communication protocol (e.g., TCP/IP).

It should be appreciated that the invention is not limited to executing on any particular system or group of systems. Also, it should be appreciated that the invention is not limited to any particular distributed architecture, network, or communication protocol.

Various embodiments of the present invention may be programmed using an object-oriented programming language, such as Java, AJAX, C++, Ada, or C# (C-Sharp). Other object-oriented programming languages, such as Ruby on Rails, Python, may also be used. Alternatively, functional, scripting, and/or logical programming languages may be used. Various aspects of the invention may be implemented in a non-programmed environment (e.g., documents created in HTML, XML, PHP, CSS or other format that, when viewed in a window of a browser program, render aspects of a graphical-user interface (GUI) or perform other functions). Various aspects of the invention may be implemented as programmed or non-programmed elements, or any combination thereof.

Various aspects of this system can be implemented by one or more systems within the computer system. For instance, the system may be a distributed system (e.g., client server, multi-tier system). In one example, the system includes software processes executing on a system associated with a user (e.g., a client system). These systems may permit the user to register, answer challenge questions, submit free form opinion information, request a drug protocol development project, review user submission, evaluate user submission, etc. Further, client systems can be associated with registered users who access, for example, a curated environment for open development of clinical trials.

Figure 17:
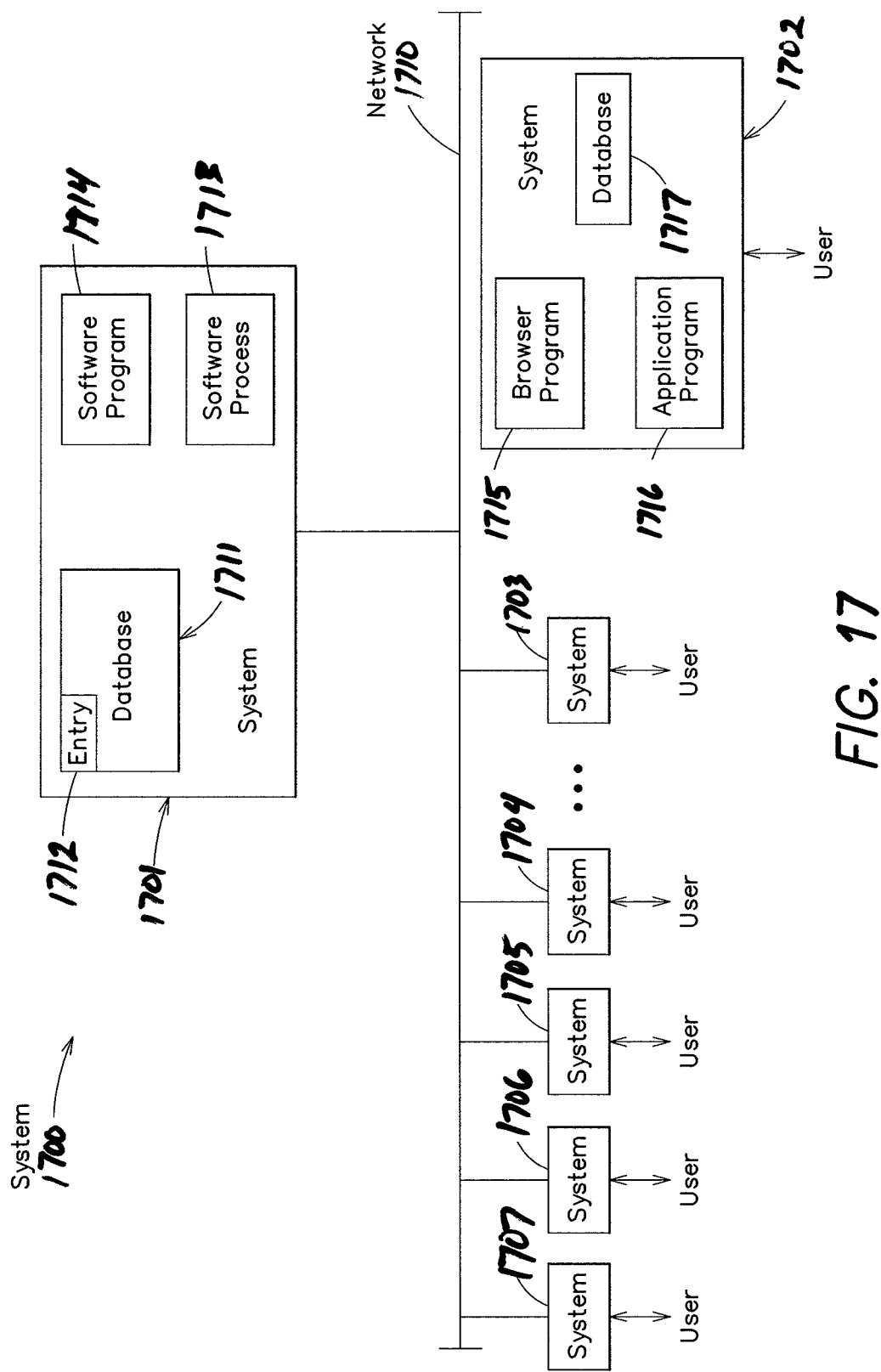
FIG. 17 is a block diagram of one example of a computer system that may be used to perform processes and functions disclosed herein.

FIG. 17 shows an architecture diagram of an example system according to one embodiment of the invention. It should be appreciated that FIG. 17 is used for illustration purposes only, and that other architectures may be used to facilitate one or more aspects of the present invention.

As shown in FIG. 17, a distributed system 1700 can include a plurality of general purpose computer system (e.g., 1701-1707) specially configured to conduct functions of a protocol builder system, including, but limited to, generation, monitoring, and evaluation of challenge questions, recruitment, information polling for protocol development information, automatic matching, automatic submission evaluation, etc. The distributed system 1700 may include one or more general purposed computer systems (e.g., 1701-1707) coupled by a communication network 1710. Such computer systems may be, for example, general-purpose computer systems as discussed above with reference to FIG. 16.

In one embodiment of the present invention, a system 1701 stores attributes associated with drug protocol development projects, collected information on protocol development, and collected registration information for users on one or more databases 1711. Each drug protocol development project can be associated with an entry 1712 in the database, although other database models can be used. In some examples, a relational database model is implemented, and in others, non-relational database models can be employed.

Further, the system 1701 performs associated functions with the displaying, classifying and evaluating of challenge question submissions, among other operations. The system 1701 can also be configured to provide access to information associated with current drug protocol development projects, completed projects, polled protocol development information, matching users, matching protocols, and can be configured to display any information through a user interface accessible over a communication network 1710, for example, the Internet.

The system 1701 may include a server process 1713 that responds to requests from one or more client programs. Process 1713 may include, for example, an HTTP server or other server-based process (e.g., a database server process, XML server, peer-to-peer process) that interfaces to one or more client programs distributed among one or more client systems, for example 1702-1707, to provide access to information on protocol development projects.

According to one embodiment, client programs may be capable of permitting a user to create, submit, alter, monitor, and comment on challenge questions and protocol development projects within an online user interface. Such client programs may include, for example, any type of operating system and/or application program capable of communicating with the system through a network. In one particular instance, a client may include a browser program (e.g., browser program) that communicates with server process using one or more communication protocols (e.g., HTTP over a TCP/IP-based network, XML requests using HTTP through an Ajax client process, distributed objects, https, or other secure or non-secure communication protocol).

Although it is shown by way of example that a browser program (e.g. 1715) may be used to access a protocol builder system by users to perform functions for developing drug protocols, it should be appreciated that other program types may be used to interface a user to server process 1713 or a protocol builder system. For instance, an application program 1713 that is specially-developed to manage drug protocol development may be provided to permit a user to participate in a project, answer challenge questions, etc., according to various embodiments of the present invention. A client program may be, for example, a thin client including an interface for submitting and monitoring challenge questions, and/or drug protocol development projects. Alternatively, the client may be a scripted program, or any other type of program having the capability of transferring data. According to one embodiment, such client programs may, for example, be downloaded and installed over the network. Further, these client programs may be stored and distributed by system in the form of one or more software programs, including for example, browser plug-ins, active x objects, applets, and java code. Clients programs can also include executable programs downloaded and installed onto a host computer (e.g. mobile phone, tablet, laptop, desktop, etc.). In some embodiments, the client programs can be configured to deliver tele-medicine operations, including for example, patient diagnosis and/or patient diagnostics. In one embodiment, the client program is configured to transmit medical, imaging, and/or heath informatics data from a host computer to a protocol builder system.

In some examples, a mobile device can download and install an executable program. The executable program can be configured to receive user input regarding ongoing study protocols. In one example, the executable program can be configured to track data regarding defined end-points for a study protocol. The data can include preliminary results in a clinical setting, patient responses to a treatment, etc. The collected data can be reviewed by the protocol builder system to validate a protocol, and/or can also be used to determine awards to participating users. In some embodiments, the executable program can also be configured to notify an end user of updates to a given protocol development project.

In one example, the client program may include an application program 1716 that permits submission of challenge response, user registration, and monitoring of protocol development. This program, in one embodiment, may be integrated with browser program 1715 executing on, for example, system 1702. For instance, the application program may include one or more controls that, when selected by the user, perform functions for manipulating submitted challenge responses. These controls may be written in a variety of programming languages, and the invention is not limited to any particular language. In one specific example, the control may be a link that, when selected, performs one or more programmed functions. Such functions may permit the user to create, submit, view, monitor, register and alter challenge submissions to the protocol builder system.

Information can be stored locally on the database 1717 and may include, for example, real-time project development information, user entered submissions, notification messages, user profile information, current protocol development projects, completed protocol development projects, awards earned, pending awards, and other information that can be used to facilitate the development of clinical study protocols.

This information may be collected from the user in an interface (e.g., as presented by program 1716) and stored in the database (e.g., database 1717). Additionally, client systems 1702-1707 may store a local copy of a user's information and any pending submission within a local database associated with the client system (e.g., database 1717 located on client system 1702). However, it should be appreciated that the invention is not limited to storing information in any particular location. A client system (e.g., clients 1702-1707) may include one or more interfaces through which protocol development information may be presented to the user. In one example, protocol information and status may be presented in an interface of a browser program (e.g., browser program 1715) executing on a client computer system (e.g., system 1702).

Having thus described several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Accordingly, the foregoing description is by way of example only.

The invention claimed is:

1. A drug development system implementing a transparent clinical protocol development model, the system comprising:
at least one processor operatively connected to a memory, the at least one processor when executing provides:
a protocol builder subsystem configured to:
display a user interface configured to:
accept a first user request for protocol development to create at least the portion of the clinical trial protocol;
prompt the first user to specify a disease, one or more drugs, and a treatment regimen for the one or more drugs to be tested;
accept input of an overview of the protocol requested;
display prompts for first user input of any known objective for the protocol;
wherein the protocol builder subsystem is further configured to:
identify, responsive to submission of the request for protocol development, for inclusion in the request review criteria to evaluate responsive submissions to the request for protocol development;
identify for inclusion in the request for protocol development, testable targets during and at a completion of the protocol for the treatment regimen, including a measureable baseline and treatment characteristics, and further including:
dependent and independent variables for the protocol;
a relationship between the independent and dependent variables; or
a change in the independent variable and an effect on the dependent variable;
publish the request for protocol development for review by the plurality of users;
create at least a portion of a clinical trial for testing at least one drug or a use of the at least one drug, the at least one portion once defined, can be used to test the at least one drug on patients during subsequent execution of a complete clinical trial and wherein the complete clinical study protocol represents a collection of aspects of a scientific experiment for testing the at least one drug with human subjects, wherein the protocol builder subsystem is configured to define parameters of at least the portion of the clinical trial responsive to interactive input from users including at least clinicians or physicians and potential patients to increase a knowledge base associated with protocol development, wherein the at least the clinicians or physicians and the potential patients define, accept, and modify the parameters of the clinical trial for testing one or more drugs;
present candidate parameters through the user interface for acceptance by the users including at least the clinicians or the physicians and the potential patients;
the user interface being further configured to:
receive a plurality of submissions regarding the candidate parameters, including at least analysis by potential patients of any member of a group or combination of members of the group comprising: clinical endpoints, inclusion criteria, exclusion criteria, dosing, and data analysis used to create at least the portion of the clinical trial, and wherein the plurality of submissions confirm, modify, and define the at least one aspect of the clinical trial for the at least one drug;
display, within the interface, the plurality of submissions from the plurality of users for subsequent review responsive to receipt of the plurality of submissions;
display modifications to the clinical endpoints, inclusion criteria, exclusion criteria, dosing, and data analysis responsive to receiving the plurality of submissions;
wherein the protocol builder subsystem is further configured to resolve the plurality of submissions from the users received regarding the candidate parameters to define the parameters and criteria for evaluating the parameters of the clinical trial;
finalize, responsive to resolving the plurality of submissions, the criteria for executing the at least the portion of the clinical trial; and
wherein the protocol builder subsystem is configured to publish the input within the interface, including the clinical endpoints, the inclusion criteria, the exclusion criteria, the dosing, and the data analysis, finalized parameters, and finalized criteria for the parameters of the clinical trial for subsequent execution of the clinical endpoints, inclusion criteria, exclusion criteria, dosing, and data analysis; and
a drug development subsystem comprising a drug development engine configured to manage execution of the finalized parameters of the clinical trial created and communicated via the protocol builder subsystem, wherein the drug development engine includes:
a collection component configured to:
receive, via a communication interface, remote trial execution data from patient monitoring devices according to at least one parameter of the clinical trial;
control execution of the patient monitoring devices according to the finalized criteria for executing the at least the portion of the clinical trial communicated by the communication interface;
receive, via a communication interface, at least health and treatment information from a patient population defined for the clinical trial wherein members of the patient population are associated with at least one patient monitoring device;
wherein drug development subsystem is further configured to associate members of the patient population with physical patient monitoring devices for issuance;
a user interface configured to publish at least a portion of the trial execution data received from the patient monitoring devices for review on the drug development system, and wherein the user interface is further configured to:
accept user input regarding the at least the portion of the trial execution data;
publish, within the interface, the user input regarding the at least the portion of the trial execution data; and
wherein the drug development subsystem is further configured to:
alter at least one parameter defined for executing the clinical trial responsive, at least in part, to the user input and remote trial execution data, and
update control and execution of the patient monitoring devices according to the alterations made to the at least one parameter defined for executing the clinical trial based upon communicating the updates over the communication interface to the patient monitoring devices.

2. The system according to claim 1, wherein the user interface includes a registration component configured to register a plurality of users including at least patients and trial investigators.

3. The system according to claim 1, wherein the protocol builder subsystem is configured to generate survey questions presented to the plurality of registered users to define at least one parameter of the clinical trial.

4. The system according to claim 3, wherein the survey questions are configured to define patient priorities regarding clinical end-points for execution of the clinical trial.

5. The system according to claim 4, wherein the protocol builder subsystem is further configured to define at least one clinical end-point parameter responsive to the patient priorities established by the survey questions.

6. The system according to claim 3, wherein the survey questions are configured to define researcher priorities regarding clinical end-points for execution of the clinical trial.

7. The system according to claim 6, wherein the protocol builder subsystem is further configured to define at least one clinical end-point parameter responsive to the researcher priorities established by the survey questions.

8. The system according to claim 1, wherein the user interface component is configured to publish the at least the portion of the trial execution data for review on the drug development system during execution of the clinical trial.

9. The system according to claim 1, further comprising an analysis component configured to aggregate the remote trial execution data to generate the at least the portion of the remote trial execution data.

10. The system according to claim 1, further comprising a storage component configured to store remote trial execution data with an associated patient.

11. The system according to claim 10, wherein the user interface is configured to display the remote trial execution data associated with the patient to the patient responsive to authentication.

12. The system according to claim 1, wherein the user interface is configured to accept user submissions regarding the at least the portion of the remote trial execution data.

13. The system according to claim 12, wherein the user interface is configured to publish the user submissions regarding the at least the portion of the remote trial execution data.

14. The system according to claim 12, further comprising an analysis component configured to identify indicators for altering at least one parameter defined for the clinical trial, responsive, at least in part, to the user submissions.

15. The system according to claim 14, wherein the analysis component is configured to identifying indicators for terminating the execution of the clinical trial early responsive, at least in part, to one or more of the user submissions and the remote execution data.

16. A computer implemented method for transparent drug development, the method comprising:
    defining, by a computer system, a clinical trial for testing at least one drug or a use of the at least one drug, the at least one portion once defined, can be used to test the at least one drug on patients during subsequent execution of a complete clinical trial and wherein the complete clinical study protocol represents a collection of aspects of a scientific experiment for testing the at least one drug with human subjects, wherein defining the clinical trial includes defining parameters of at least the portion of the clinical trial responsive to input from users and responsive to interactive input from users including at least clinicians or physicians and potential patients to increase a knowledge base associated with protocol development, wherein the at least the clinicians or physicians and the potential patients define, accept, and modify the parameters of the clinical trial for testing one or more drugs;
    presenting, by the computer system hosting the protocol builder subsystem through a user interface, candidate parameters for acceptance by the users including at least the clinicians or the physicians and the potential patients,
    receiving, by the user interface, a plurality of submissions regarding the candidate parameters, including at least analysis by potential patients of any member of a group or combination of members of the group comprising: clinical endpoints, inclusion criteria, exclusion criteria, dosing, and data analysis used to create at least the portion of the clinical trial, and wherein the plurality of submissions confirm, modify, and define the at least one aspect of the clinical trial for the at least one drug;
    displaying, by the user interface, the plurality of submissions from the plurality of users for subsequent review responsive to receipt of the plurality of submissions;
    displaying, by the user interface, modifications to the clinical endpoints, inclusion criteria, exclusion criteria, dosing, and data analysis responsive to receiving the plurality of submissions;
    resolving, by the computer system, the plurality of submissions from the users received on the candidate parameters to define the parameters and criteria for evaluating the parameters of the clinical trial;
    finalizing, responsive to resolving the plurality of submissions, the criteria for executing the at least the portion of the clinical trial;
    publishing, by the computer system, the input on the clinical endpoints, the inclusion criteria, the exclusion criteria, the dosing, and the data analysis finalized parameters, finalized criteria for the parameters of the clinical trial for review on the computer system;
    managing, by a computer system hosting a drug development subsystem, execution of the parameters of the clinical trial, wherein managing execution includes:
        receiving, via a communication interface, remote trial execution data from at least health and treatment monitoring devices associated with a patient population defined for the clinical trial wherein each member of the patient population is associated with at least one patient monitoring device;
        control execution of the patient monitoring devices according to the finalized criteria for executing the at least the portion of the clinical trial communicated by the communication interface;
    associating, by the computer system, members of the patient population with physical patient monitoring devices;
    publishing, by the computer system, at least a portion of the remote trial execution data and data received from the patient monitoring devices for review on the drug development system, and user input regarding the at least the portion of the trial execution data; and
    altering, by the computer system, at least one parameter defined for executing the clinical trial responsive, at least in part, to the user input and remote trial execution data; and
    updating and controlling, by the computer system, execution of the patient monitoring devices according to the alterations made to the at least one parameter defined for executing the clinical trial based upon communicating the updates over the communication interface to the patient monitoring devices.

17. The method according to claim 16, wherein publishing, by the computer system, at least a portion of the remote trial execution data includes publishing the at least the portion of the remote trial execution data during execution of the clinical trial.

18. The method according to claim 17, further comprising aggregating, by the computer system, the execution data to generate the at least the portion of the remote trial execution data for review.

19. The method according to claim 16, further comprising:
    generating survey questions presented to a plurality of users; and
    defining at least one parameter of the clinical trial responsive to answers to the survey questions.

20. The method according to claim 19, wherein the survey questions are configured to define patient priorities regarding clinical end-points for execution of the clinical trial.

21. The method according to claim 20, wherein defining the at least one parameter of the clinical trial responsive to answers to the survey questions includes defining the at least one clinical end-point parameter responsive to the patient priorities established by the survey questions.

22. The method according to claim 19, wherein the survey questions are configured to define researcher priorities regarding clinical end-points for execution of the clinical trial.

23. The method according to claim 22, wherein defining the at least one parameter of the clinical trial responsive to answers to the survey questions includes defining the at least one clinical end-point parameter responsive to the researcher priorities established by the survey questions.

24. The method according to claim 16, further comprising:
    identifying a clinical trial patient responsive to user input; and
    presenting the remote trial execution data associated with the clinical trial patient responsive to identification.

25. The method according to claim 16, further comprising:
    accepting user submissions regarding the at least the portion of the remote trial execution data.

26. The method according to claim 25, further comprising publishing, by the computer system, the user submissions regarding the portion of the remote trial execution data for review on the drug development system.

27. The method according to claim 26, further comprising altering at least one parameter defined for the clinical trial responsive, at least in part, to the user submissions.

28. The method according to claim 26, further comprising identifying indicators for terminating the execution of the clinical trial early responsive, at least in part, to one or more of the user submissions and the remote execution data.

29. The method according to claim 16, further comprising managing, by the computer system, virtual interviews between clinical investigators and the clinical trial population according to the parameters of the clinical trial.

30. A drug development system implementing a transparent clinical protocol development model, the system comprising:
- a protocol builder subsystem for open clinical study protocol creation wherein the protocol builder system provides for interactive real time input of a plurality of participants including at least clinicians or physicians and potential patients to create at least a portion of a clinical trial for testing one or more drugs, that once defined can be used to test the drug on patients during subsequent execution of a complete clinical trial, wherein the protocol builder subsystem comprises:
  - at least one processor operatively connected to a memory;
  - a first user interface, executed by the at least one processor, configured to:
    - accept a first user request for protocol development to create at least the portion of the clinical trial protocol;
    - prompt the first user to specify a disease, one or more drugs, and a treatment regimen for the one or more drugs to be tested;
    - accept input of an overview of the protocol requested;
    - display prompts for first user input of any known objective for the protocol;
  - wherein the protocol builder subsystem is further configured to:
    - identify, responsive to submission of the request for protocol development, for inclusion in the request review criteria to evaluate responsive submissions to the request for protocol development;
    - identify for inclusion in the request for protocol development, testable targets during and at a completion of the protocol for the treatment regimen, including a measureable baseline and treatment characteristics, and further including:
      - dependent and independent variables for the protocol;
      - a relationship between the independent and dependent variables; or
      - a change in the independent variable and an effect on the dependent variable;
    - publish the request for protocol development for review by the plurality of users;
  - a second user interface configured to register a plurality of users for access to a curated environment, wherein the plurality of users include at least clinicians or physicians and potential patients to increase a knowledge base associated with protocol development, wherein the second user interface is further configured to provide access to at least one protocol development project over a communication network, wherein each respective one of the at least one protocol development project defines criteria for executing the clinical trial and wherein a complete clinical study protocol represents the collection of aspects of a scientific experiment for testing the one or more drugs with human subjects;
  - a challenge generation component configured to identify candidate challenges for protocol development, wherein each candidate challenge is configured to define at least one aspect of the clinical trial for a drug;
  - an evaluation component configured to present candidate challenges for acceptance, wherein the evaluation component is further configured to receive approval for at least some of the candidate challenges;
  - wherein the second user interface is further configured to:
    - execute iterative development of candidate challenges, the execution including requests for responses from the users including at least clinicians or physicians and potential patients, wherein the responses confirm, modify, or define the at least one aspect of the clinical trial for a drug associated with a candidate challenge;
    - accept a plurality of submissions from the plurality of users in response to presentation of the candidate challenges and the requests for responses;
    - display the plurality of submissions from the plurality of users for review by subsequent users responsive to receipt;
    - display modifications to the candidate challenges responsive to receiving the plurality of submissions; and
  - wherein the protocol builder subsystem is further configured to:
    - finalize, using the at least one processor, for each respective one of the at least one protocol development project, the criteria for executing at least a portion of the clinical trial responsive to review information received and responses to the candidate challenges based on at least the review information received, the modifications to the candidate challenges, and any other responses to the candidate challenges;
    - communicate the finalized criteria for executing at least a portion of the clinical trial protocol to a drug development subsystem; and
- the drug development subsystem comprising a drug development engine configured to manage execution of the criteria for executing at least a portion of the clinical trial protocol wherein created via the protocol builder subsystem, wherein the drug development engine includes:
  - a collection component configured to:
    - control execution of patient monitoring devices according to at least one parameter of the clinical trial defined by the criteria for executing at least a portion of the clinical trial protocol;
    - receive remote trial execution data from the patient monitoring devices, wherein the collection component is configured to receive at least health and treatment information from a patient population defined for the clinical trial, wherein members of the patient population are associated with at least one patient monitoring device;

wherein the drug development subsystem is further configured to associate members of the patient population with physical patient monitoring devices for issuance;
a third user interface configured to:
publish at least a portion of the trial execution data received from the patient monitoring devices for review on the drug development system,
accept user input regarding the at least the portion of the trial execution data,
display user input regarding the at least the portion of the trial execution data;
display alterations at least one parameter defined for executing the clinical trial,
wherein the drug development subsystem is further configured to:
alter at least one parameter defined for executing the clinical trial, responsive, at least in part, to the user input and remote trial execution data received from the patient population; and
update control and execution of the patient monitoring devices according to the alterations made to the at least one parameter defined for executing the clinical trial based upon communicating the updates over the communication interface to the patient monitoring devices.

* * * * *